US008894661B2

(12) United States Patent
McDevitt et al.

(10) Patent No.: US 8,894,661 B2
(45) Date of Patent: Nov. 25, 2014

(54) HELICOIL INTERFERENCE FIXATION SYSTEM FOR ATTACHING A GRAFT LIGAMENT TO A BONE

(75) Inventors: Dennis McDevitt, Raleigh, NC (US); Vincent Novak, Longmont, CO (US)

(73) Assignee: Smith & Nephew, Inc., Andover, MA (US)

( * ) Notice: Subject to any disclaimer, the term of this patent is extended or adjusted under 35 U.S.C. 154(b) by 515 days.

(21) Appl. No.: 12/392,804

(22) Filed: Feb. 25, 2009

(65) Prior Publication Data

US 2009/0319043 A1 Dec. 24, 2009

Related U.S. Application Data

(63) Continuation-in-part of application No. 11/893,440, filed on Aug. 16, 2007, now abandoned.

(60) Provisional application No. 61/200,285, filed on Nov. 26, 2008.

(51) Int. Cl.
*A61B 17/58* (2006.01)
*A61B 17/60* (2006.01)
*A61F 2/00* (2006.01)
*A61B 17/88* (2006.01)
*A61B 17/86* (2006.01)
*A61B 17/80* (2006.01)
*A61F 2/28* (2006.01)
*A61F 2/08* (2006.01)
*A61F 2/30* (2006.01)
*A61F 2/38* (2006.01)
*A61B 17/04* (2006.01)

(52) U.S. Cl.
CPC ....... *A61F 2/0811* (2013.01); *A61F 2002/2817* (2013.01); *A61F 2/08* (2013.01);

(Continued)

(58) Field of Classification Search
USPC ............ 606/304, 54, 60, 286, 310, 104, 321, 606/99, 72, 73, 300, 323, 314, 316, 78; 411/438, 452, 16; 81/459, 436
See application file for complete search history.

(56) References Cited

U.S. PATENT DOCUMENTS 3,499,222 A 3/1970 Linkow et al.
3,869,942 A 3/1975 DeCaro (Continued)

FOREIGN PATENT DOCUMENTS

CN 1829479 A 9/2006
CN 101031248 A 9/2007

(Continued)

OTHER PUBLICATIONS

Smith & Nephew brochure titled "BioRCITM Bioabsorbable Screws: Anatomically Targeted Screws for ACL and PCL Reconstruction", 2000.

(Continued)

*Primary Examiner* — David Bates
*Assistant Examiner* — Samuel Hanna
(74) *Attorney, Agent, or Firm* — Burns & Levinson LLP; Joseph M. Maraia

(57) ABSTRACT

A helicoil interference fixation system comprising:
a helicoil comprising a helical body comprising a plurality of turns separated by spaces therebetween, the helical body terminating in a proximal end and a distal end, and at least one internal strut extending between at least two turns of the helical body; and
an inserter for turning the helicoil, the inserter comprising at least one groove for receiving the at least one strut; the helicoil being mounted on the inserter such that the at least one strut of the helicoil is mounted in the at least one groove of the inserter, such that rotation of the inserter causes rotation of the helicoil.

8 Claims, 30 Drawing Sheets

(52) U.S. Cl.
CPC .......... *A61F 2002/0858* (2013.01); *A61F 2002/30062* (2013.01); *A61F 2/30744* (2013.01); *A61F 2002/30593* (2013.01); *A61F 2002/30772* (2013.01); *A61F 2002/30736* (2013.01); *A61F 2310/00017* (2013.01); *A61B 17/8886* (2013.01); *A61B 17/869* (2013.01); *A61F 2002/3085* (2013.01); *A61B 17/861* (2013.01); *A61F 2210/0004* (2013.01); *A61F 2230/0093* (2013.01); *A61F 2230/0082* (2013.01); *A61F 2220/0025* (2013.01); *A61F 2/0805* (2013.01); *A61F 2002/2835* (2013.01); *A61F 2002/30329* (2013.01); *A61B 17/8877* (2013.01); *A61B 17/809* (2013.01); *A61F 2/389* (2013.01); *A61F 2002/30299* (2013.01); *A61F 2002/0841* (2013.01); *A61B 2017/0441* (2013.01); *A61F 2002/30266* (2013.01)
USPC .......... 606/104; 606/99; 606/301; 606/304; 606/308

(56) References Cited

U.S. PATENT DOCUMENTS

| | | | |
|---|---|---|---|
| 4,177,797 A | | 12/1979 | Baylis et al. |
| 4,653,489 A | | 3/1987 | Tronzo |
| 4,834,757 A | | 5/1989 | Brantigan |
| 4,854,311 A | | 8/1989 | Steffee |
| 4,913,143 A | | 4/1990 | Oloff et al. |
| 4,961,740 A | | 10/1990 | Ray et al. |
| 5,026,373 A | * | 6/1991 | Ray et al. ............... 606/86 A |
| 5,055,104 A | | 10/1991 | Ray |
| 5,116,337 A | | 5/1992 | Johnson |
| 5,129,904 A | | 7/1992 | Illi |
| 5,129,906 A | | 7/1992 | Ross et al. |
| 5,197,967 A | | 3/1993 | Wilson |
| 5,236,431 A | | 8/1993 | Gogolewski et al. |
| 5,242,447 A | | 9/1993 | Borzone |
| 5,354,299 A | * | 10/1994 | Coleman ............... 606/916 |
| 5,364,400 A | | 11/1994 | Rego, Jr. et al. |
| 5,383,878 A | | 1/1995 | Roger et al. |
| 5,407,427 A | | 4/1995 | Zhu et al. |
| 5,411,523 A | | 5/1995 | Goble |
| 5,447,533 A | | 9/1995 | Vachon et al. |
| 5,464,427 A | | 11/1995 | Curtis et al. |
| 5,470,334 A | | 11/1995 | Ross et al. |
| 5,531,780 A | | 7/1996 | Vachon |
| 5,571,139 A | | 11/1996 | Jenkins, Jr. |
| 5,593,409 A | | 1/1997 | Michelson |
| 5,609,635 A | | 3/1997 | Michelson |
| 5,626,613 A | | 5/1997 | Schmieding |
| 5,645,547 A | | 7/1997 | Coleman |
| 5,658,285 A | | 8/1997 | Marnay et al. |
| 5,676,545 A | | 10/1997 | Jones |
| 5,681,352 A | | 10/1997 | Clancy, III et al. |
| 5,688,285 A | | 11/1997 | Yamada |
| 5,695,497 A | * | 12/1997 | Stahelin ............... 606/916 |
| 5,709,683 A | | 1/1998 | Bagby |
| 5,802,794 A | | 9/1998 | Robson |
| 5,833,715 A | | 11/1998 | Vachon et al. |
| 5,888,227 A | | 3/1999 | Cottle |
| 5,891,146 A | | 4/1999 | Simon et al. |
| 5,921,982 A | | 7/1999 | Lesh et al. |
| 5,951,560 A | | 9/1999 | Simon et al. |
| 5,961,524 A | | 10/1999 | Crombie |
| 5,964,783 A | | 10/1999 | Grafton et al. |
| 5,968,047 A | | 10/1999 | Reed |
| 5,968,098 A | | 10/1999 | Winslow |
| 5,984,967 A | | 11/1999 | Zdeblick et al. |
| 6,008,433 A | | 12/1999 | Stone |
| 6,039,762 A | | 3/2000 | McKay |
| 6,086,593 A | | 7/2000 | Bonutti |
| 6,096,060 A | | 8/2000 | Fitts et al. |
| 6,097,986 A | | 8/2000 | Janke et al. |
| 6,196,780 B1 | | 3/2001 | Wakai et al. |
| 6,235,057 B1 | | 5/2001 | Roger et al. |
| 6,283,973 B1 | | 9/2001 | Hubbard et al. |
| 6,360,129 B1 | | 3/2002 | Ley et al. |
| 6,443,989 B1 | | 9/2002 | Jackson |
| 6,447,545 B1 | | 9/2002 | Bagby |
| 6,488,683 B2 | | 12/2002 | Lieberman |
| 6,514,257 B2 | | 2/2003 | Dovesi et al. |
| 6,517,542 B1 | | 2/2003 | Papay et al. |
| 6,527,774 B2 | | 3/2003 | Lieberman |
| 6,544,265 B2 | | 4/2003 | Lieberman |
| 6,551,319 B2 | | 4/2003 | Lieberman |
| 6,551,320 B2 | | 4/2003 | Lieberman |
| 6,551,322 B1 | | 4/2003 | Lieberman |
| 6,554,830 B1 | | 4/2003 | Chappius |
| 6,589,245 B1 | | 7/2003 | Weiler et al. |
| 6,626,917 B1 | | 9/2003 | Craig |
| 6,823,871 B2 | | 11/2004 | Schmieding |
| 6,855,168 B2 | | 2/2005 | Crozet |
| 6,863,671 B1 | | 3/2005 | Strobel et al. |
| 6,953,462 B2 | | 10/2005 | Lieberman |
| 7,033,372 B1 | | 4/2006 | Cahalan |
| 7,070,586 B2 | | 7/2006 | Hart et al. |
| 7,083,647 B1 | | 8/2006 | Sklar et al. |
| 7,189,251 B2 | | 3/2007 | Kay |
| 7,195,634 B2 | | 3/2007 | Schmieding et al. |
| 7,217,279 B2 | | 5/2007 | Reese |
| 7,594,929 B2 | | 9/2009 | Collette |
| 7,608,098 B1 | | 10/2009 | Stone et al. |
| 7,867,252 B2 | | 1/2011 | Criscuolo et al. |
| 7,914,539 B2 | | 3/2011 | Stone et al. |
| 8,016,865 B2 | | 9/2011 | Donnelly et al. |
| 8,034,090 B2 | | 10/2011 | Stone et al. |
| 8,636,799 B2 | | 1/2014 | Sklar et al. |
| 2002/0022862 A1 | | 2/2002 | Grafton et al. |
| 2002/0055737 A1 | | 5/2002 | Lieberman |
| 2002/0055738 A1 | | 5/2002 | Lieberman |
| 2002/0055742 A1 | | 5/2002 | Lieberman |
| 2002/0087190 A1 | | 7/2002 | Benavitz et al. |
| 2002/0099382 A1 | | 7/2002 | Salazar et al. |
| 2002/0143335 A1 | * | 10/2002 | von Hoffmann et al. ....... 606/67 |
| 2002/0165546 A1 | | 11/2002 | Goble et al. |
| 2003/0055431 A1 | | 3/2003 | Brannon |
| 2003/0065374 A1 | | 4/2003 | Honeck |
| 2003/0069640 A1 | | 4/2003 | Ferreira et al. |
| 2003/0125749 A1 | * | 7/2003 | Yuan et al. ............... 606/104 |
| 2003/0181913 A1 | | 9/2003 | Lieberman |
| 2004/0015170 A1 | | 1/2004 | Tallarida et al. |
| 2004/0030343 A1 | | 2/2004 | Kurc |
| 2004/0039404 A1 | | 2/2004 | Dreyfuss |
| 2004/0073216 A1 | | 4/2004 | Lieberman |
| 2004/0097945 A1 | * | 5/2004 | Wolf ............... 606/73 |
| 2004/0122424 A1 | | 6/2004 | Ferree |
| 2004/0143158 A1 | | 7/2004 | Hart et al. |
| 2004/0143237 A1 | | 7/2004 | Hart et al. |
| 2004/0153074 A1 | | 8/2004 | Bojarski et al. |
| 2004/0267265 A1 | | 12/2004 | Kyle |
| 2005/0107828 A1 | | 5/2005 | Reese |
| 2005/0159727 A1 | | 7/2005 | Lesh |
| 2005/0222681 A1 | | 10/2005 | Richley et al. |
| 2005/0234458 A1 | | 10/2005 | Huebner |
| 2005/0250984 A1 | | 11/2005 | Lam et al. |
| 2005/0250985 A1 | | 11/2005 | Saadat et al. |
| 2005/0250987 A1 | | 11/2005 | Ewers et al. |
| 2005/0250988 A1 | | 11/2005 | Ewers et al. |
| 2005/0283239 A1 | | 12/2005 | Crozet |
| 2006/0009769 A1 | | 1/2006 | Lieberman |
| 2006/0030948 A1 | | 2/2006 | Manrique et al. |
| 2006/0079895 A1 | | 4/2006 | McLeer |
| 2006/0100627 A1 | | 5/2006 | Stone et al. |
| 2006/0106390 A1 | * | 5/2006 | Jensen et al. ............... 606/73 |
| 2006/0142769 A1 | | 6/2006 | Collette |
| 2006/0149266 A1 | | 7/2006 | Cordasco |
| 2006/0217681 A1 | | 9/2006 | Hart et al. |
| 2006/0241636 A1 | | 10/2006 | Novak et al. |
| 2006/0247642 A1 | * | 11/2006 | Stone et al. ............... 606/73 |
| 2006/0253080 A1 | | 11/2006 | Tulleken et al. |
| 2006/0276841 A1 | | 12/2006 | Barbieri et al. |
| 2007/0032797 A1 | | 2/2007 | Ortiz et al. |
| 2007/0093895 A1 | | 4/2007 | Donnelly et al. |

(56) References Cited

U.S. PATENT DOCUMENTS

| | | |
|---|---|---|
| 2007/0122764 A1 | 5/2007 | Balfour et al. |
| 2007/0142849 A1 | 6/2007 | Ewers et al. |
| 2007/0185532 A1 | 8/2007 | Stone et al. |
| 2007/0198019 A1 | 8/2007 | Schomer et al. |
| 2008/0027446 A1 | 1/2008 | Stone et al. |
| 2008/0065114 A1 | 3/2008 | Stone et al. |
| 2008/0082128 A1 | 4/2008 | Stone |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0154314 A1 | 6/2008 | McDevitt |
| 2008/0179839 A1 | 7/2008 | Walters |
| 2009/0024174 A1 | 1/2009 | Stark |
| 2009/0042951 A1 | 2/2009 | Danziger |
| 2009/0076544 A1 | 3/2009 | DiMatteo et al. |
| 2009/0248029 A1 | 10/2009 | Paulos |
| 2009/0319043 A1 | 12/2009 | McDevitt et al. |
| 2010/0106166 A1 | 4/2010 | Cropper et al. |
| 2011/0112576 A1 | 5/2011 | Nguyen et al. |
| 2011/0282450 A1 | 11/2011 | Donnelly et al. |
| 2011/0319933 A1 | 12/2011 | Tepic |
| 2013/0150859 A1 | 6/2013 | Kehres et al. |
| 2013/0158596 A1 | 6/2013 | Miller et al. |
| 2013/0158597 A1 | 6/2013 | Hernandez |
| 2013/0158598 A1 | 6/2013 | Lizardi |
| 2013/0158599 A1 | 6/2013 | Hester |
| 2013/0158610 A1 | 6/2013 | Hernandez |
| 2014/0142697 A1 | 5/2014 | Sklar et al. |

FOREIGN PATENT DOCUMENTS

| | | |
|---|---|---|
| EP | 0502698 B1 | 9/1992 |
| EP | 0538895 A2 | 4/1993 |
| EP | 0 669 110 B1 | 8/1995 |
| EP | 0682917 B1 | 11/1995 |
| EP | 1 093 774 | 4/2001 |
| EP | 1147751 B1 | 10/2001 |
| EP | 1917926 A1 | 7/2008 |
| EP | 2036501 A3 | 9/2010 |
| EP | 2601894 A1 | 6/2013 |
| FR | 2760355 A1 | 9/1998 |
| FR | 2803739 A1 | 7/2001 |
| FR | 2846867 A1 | 5/2004 |
| WO | 9608205 A1 | 3/1996 |
| WO | 9619947 A1 | 7/1996 |
| WO | 9802117 A1 | 1/1998 |
| WO | 9826717 A1 | 6/1998 |
| WO | 2006/055516 A2 | 5/2006 |
| WO | 2007093192 A1 | 8/2007 |
| WO | 2008021474 A2 | 2/2008 |
| WO | WO2008021474 A2 | 2/2008 |
| WO | 2008/100944 A1 | 8/2008 |
| WO | 2009042951 A1 | 4/2009 |

OTHER PUBLICATIONS

Biomet brochure titled "Bio-CoreTM Interference Screw", 2007.
International Search Report and Written Opinion for PCT/US2009/065304 Dated Mar. 8, 2010.
Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.
International Search and Written Opinion for PCT/US2009/065304 mailed Jun. 5, 2013.
International Search and Written Opinion for PCT/US2012/041298 mailed Jun. 5, 2013.
International Search and Written Opinion for PCT/US2012/028803 mailed Oct. 24, 2010.
Notice of Reasons for Rejections for Japanese Patent Application No. 2011-538642, mailed Oct. 1, 2013.
First Office Action for Chinese Patent Application No. 200980155954.7, issued Apr. 12, 2013.
Second Office Action for Chinese Patent Application No. 200980155954.7, issued Oct. 24, 2013.
International Search Report for PCT/US2011/027837 mailed May 19, 2011.
International Search and Written Opinion for PCT/US2014/022539 mailed Jun. 27, 2014.
International Search and Written Opinion for PCT/US2014/020747 mailed Jun. 6, 2014.
Decision of Rejection for Japanese Patent Application No. 2011-538642, mailed Jun. 14, 2014.
International Search and Written Opinion for PCT/US2014/033535 mailed Jul. 18, 2014.
First Office Action for Chinese Patent Application No. 201180013194.3, issued Jul. 21, 2014.

* cited by examiner

HELICOIL INTERFERENCE FIXATION SYSTEM FOR ATTACHING A GRAFT LIGAMENT TO A BONE

REFERENCE TO PENDING PRIOR PATENT APPLICATIONS

This patent application:

(i) is a continuation-in-part of prior U.S. patent application Ser. No. 11/893,440, filed Aug. 16, 2007 now abandoned by Dennis M. McDevitt for COMPOSITE INTERFERENCE SCREW FOR ATTACHING A GRAFT LIGAMENT TO A BONE, AND OTHER APPARATUS FOR MAKING ATTACHMENTS TO BONE; and (ii) claims benefit of prior U.S. Provisional Patent Application Ser. No. 61/200,285, filed Nov. 26, 2008 by Dennis M. McDevitt et al. for HELICOIL FIXATION DEVICE.

The two above-identified patent applications are hereby incorporated herein by reference.

FIELD OF THE INVENTION

This invention relates to medical apparatus and procedures in general, and more particularly to medical apparatus and procedures for reconstructing a ligament.

BACKGROUND OF THE INVENTION

Ligaments are tough bands of tissue which serve to connect the articular extremities of bones, and/or to support and/or retain organs in place within the body. Ligaments are typically made up of coarse bundles of dense fibrous tissue which are disposed in a parallel or closely interlaced manner, with the fibrous tissue being pliant and flexible but not significantly extensible.

In many cases, ligaments are torn or ruptured as the result of an accident. Accordingly, various procedures have been developed to repair or replace such damaged ligaments.

For example, in the human knee, the anterior and posterior cruciate ligaments (i.e., the "ACL" and "PCL") extend between the top end of the tibia and the bottom end of the femur. The ACL and PCL serve, together with other ligaments and soft tissue, to provide both static and dynamic stability to the knee. Often, the anterior cruciate ligament (i.e., the ACL) is ruptured or torn as the result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such a procedure, bone tunnels are generally formed in both the top of the tibia and the bottom of the femur, with one end of the graft ligament being positioned in the femoral tunnel and the other end of the graft ligament being positioned in the tibial tunnel, and with the intermediate portion of the graft ligament spanning the distance between the bottom of the femur and the top of the tibia. The two ends of the graft ligament are anchored in their respective bone tunnels in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere within the patient's body, e.g., a patella tendon with or without bone blocks attached, a semitendinosus tendon and/or a gracilis tendon. In other circumstances, the graft ligament may be harvested from a cadaver. In still other circumstances, the graft ligament may be a synthetic device. For the purposes of the present invention, all of the foregoing may be collectively referred to herein as a "graft ligament".

As noted above, various approaches are well known in the art for anchoring the two ends of the graft ligament in the femoral and tibial bone tunnels.

In one well-known procedure, which may be applied to femoral fixation, tibial fixation, or both, the end of the graft ligament is placed in the bone tunnel, and then the graft ligament is fixed in place using a headless orthopedic screw, generally known in the art as an "interference" screw. More particularly, with this approach, the end of the graft ligament is placed in the bone tunnel and then the interference screw is advanced into the bone tunnel so that the interference screw extends parallel to the bone tunnel and simultaneously engages both the graft ligament and the side wall of the bone tunnel. In this arrangement, the interference screw essentially drives the graft ligament laterally, into engagement with the opposing side wall of the bone tunnel, whereby to secure the graft ligament to the host bone with a so-called "interference fit". Thereafter, over time (e.g., several months), the graft ligament and the host bone grow together at their points of contact so as to provide a strong, natural joinder between the ligament and the bone.

Interference screws have proven to be an effective means for securing a graft ligament in a bone tunnel. However, the interference screw itself generally takes up a substantial amount of space within the bone tunnel, which can limit the surface area contact established between the graft ligament and the side wall of the bone tunnel. This in turn limits the region of bone-to-ligament in-growth, and hence can affect the strength of the joinder. By way of example but not limitation, it has been estimated that the typical interference screw obstructs about 50% of the potential bone-to-ligament integration region.

For this reason, substantial efforts have been made to provide interference screws fabricated from absorbable materials, so that the interference screw can eventually disappear over time and bone-to-ligament in-growth can take place about the entire perimeter of the bone tunnel. To this end, various absorbable interference screws have been developed which are made from biocompatible, bioabsorbable polymers, e.g., polylactic acid (PLA), polyglycolic acid (PGA), etc. These polymers generally provide the substantial mechanical strength needed to advance the interference screw into position, and to thereafter hold the graft ligament in position while bone-to-ligament in-growth occurs, without remaining in position on a permanent basis.

In general, interference screws made from such biocompatible, bioabsorbable polymers have proven clinically successful. However, these absorbable interference screws still suffer from several disadvantages. First, clinical evidence suggests that the quality of the bone-to-ligament in-growth is somewhat different than natural bone-to-ligament in-growth, in the sense that the aforementioned bioabsorbable polymers tend to be replaced by a fibrous mass rather than a well-ordered tissue matrix. Second, clinical evidence suggests that absorption generally takes a substantial period of time, e.g., on the order of three years or so. Thus, during this absorption time, the bone-to-ligament in-growth is still significantly limited by the presence of the interference screw. Third, clinical evidence suggests that, for many patients, absorption is never complete, leaving a substantial foreign mass remaining within the body. This problem is exacerbated somewhat by the fact that absorbable interference screws generally tend to be fairly large in order to provide them with adequate strength, e.g., it is common for an interference screw to have a diameter (i.e., an outer diameter) of 8-12 mm and a length of 20-25 mm.

Thus, there is a need for a new and improved interference fixation system which (i) has the strength needed to hold the graft ligament in position while bone-to-ligament in-growth occurs, and (ii) promotes superior bone-to-ligament in-growth.

SUMMARY OF THE INVENTION

These and other objects are addressed by the provision and use of a novel helicoil interference fixation system for attaching a graft ligament to a bone.

In one preferred form of the invention, there is provided a novel helicoil interference fixation system comprising:

a helicoil comprising a helical body comprising a plurality of turns separated by spaces therebetween, the helical body terminating in a proximal end and a distal end, and at least one internal strut extending between at least two turns of the helical body; and an inserter for turning the helicoil, the inserter comprising at least one groove for receiving the at least one strut;

the helicoil being mounted on the inserter such that the at least one strut of the helicoil is mounted in the at least one groove of the inserter, such that rotation of the inserter causes rotation of the helicoil.

In another preferred form of the invention, there is provided a novel method for attaching a graft ligament to a bone, the method comprising:

providing a helicoil interference fixation system comprising:

a helicoil comprising a helical body comprising a plurality of turns separated by spaces therebetween, the helical body terminating in a proximal end and a distal end, and at least one internal strut extending between at least two turns of the helical body; and an inserter for turning the helicoil, the inserter comprising at least one groove for receiving the at least one strut;

the helicoil being mounted on the inserter such that the at least one strut of the helicoil is mounted in the at least one groove of the inserter, such that rotation of the inserter causes rotation of the helicoil;

forming a bone tunnel in the bone, and providing a graft ligament;

inserting the graft ligament into the bone tunnel; and using the inserter to turn the helicoil into the bone tunnel so as to secure the graft ligament to the bone using an interference fit.

In another preferred form of the invention, there is provided a novel helicoil comprising a helical body comprising a plurality of turns separated by spaces therebetween, the helical body terminating in a proximal end and a distal end, and at least one internal strut extending between at least two turns of the helical body, wherein the at least one internal strut comprises a helical construction.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a novel helicoil interference fixation system for attaching a graft ligament to a bone or other tissue.

For convenience, the present invention will hereinafter be discussed in the context of its use for an ACL tibial and/or femoral fixation; however, it should be appreciated that the present invention may also be used for the fixation of other graft ligaments to the tibia and/or the femur; and/or the fixation of other graft ligaments to other bones or to other tissue such as organs.

Looking first at FIGS. 1-7, there is shown a novel helicoil interference fixation system 5 for securing a graft ligament to a bone. Helicoil interference fixation system 5 generally comprises a helicoil 10 for disposition in a bone tunnel so as to hold the graft ligament in position while bone-to-ligament in-growth occurs. Helicoil interference fixation system 5 also comprises an inserter 15 for deploying helicoil 10 in the bone tunnel.

Figure 1:
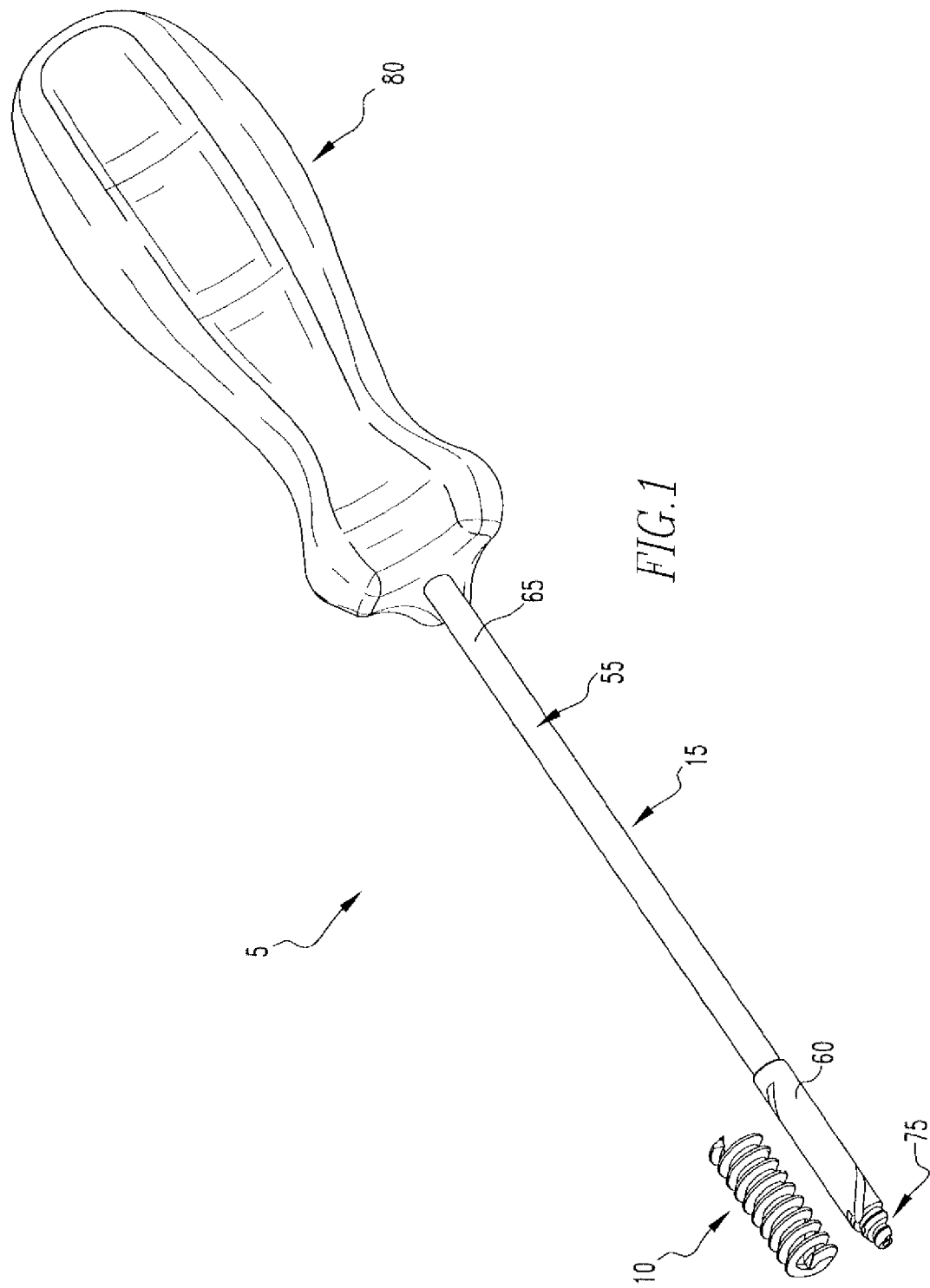
FIGS. 1-7 are schematic views showing a first helicoil interference fixation system formed in accordance with the present invention.
Figure 2:
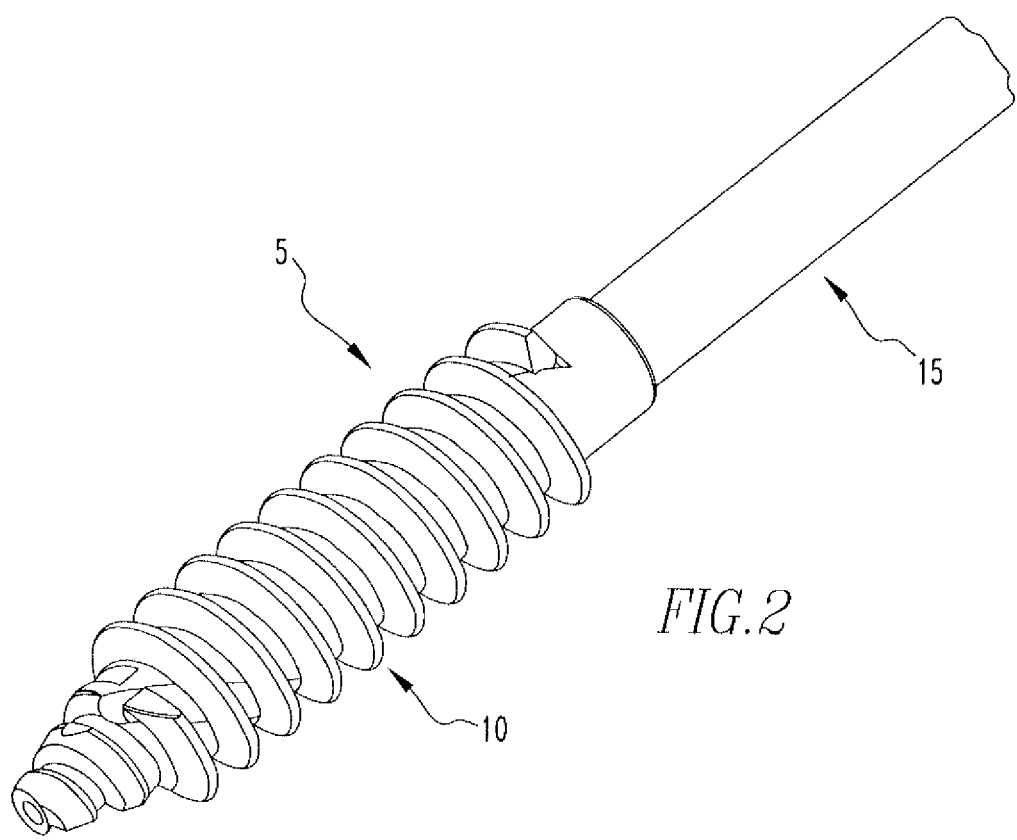
Figure 3:
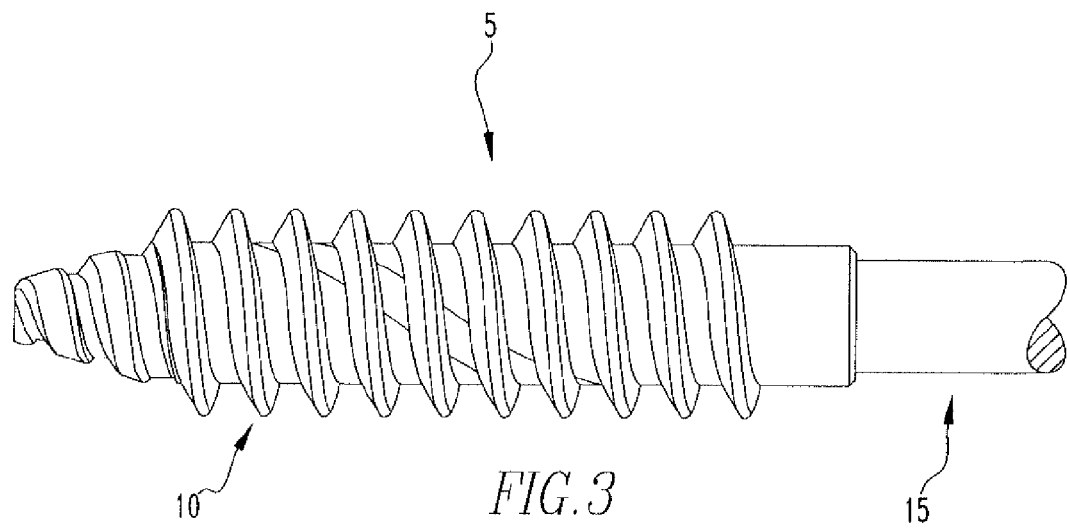
Figure 4:
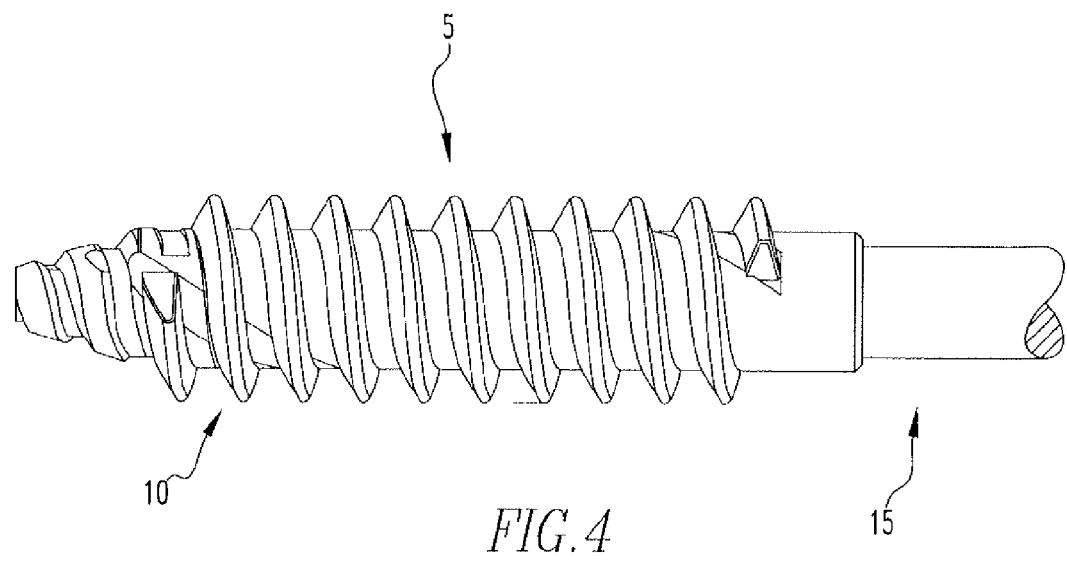
Figure 5:
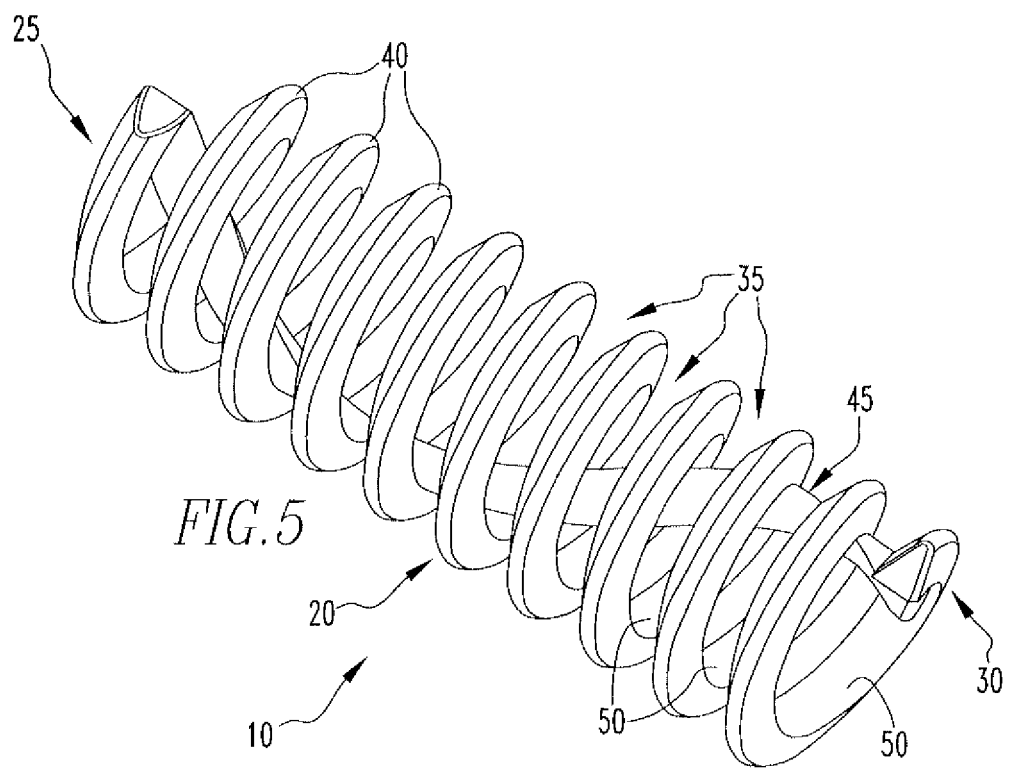
Figure 6:
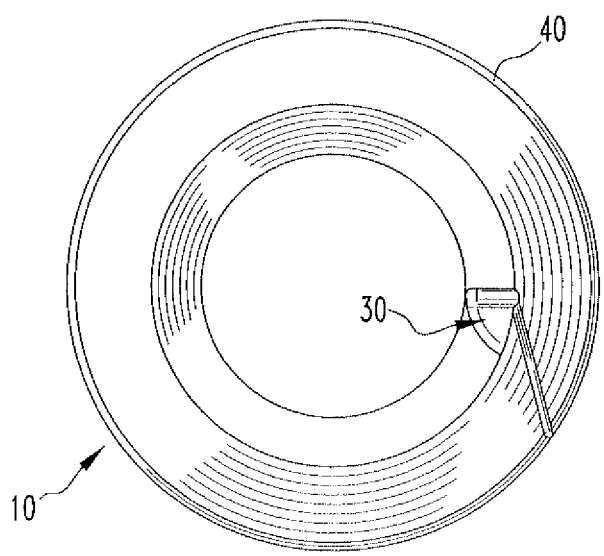
Figure 7:
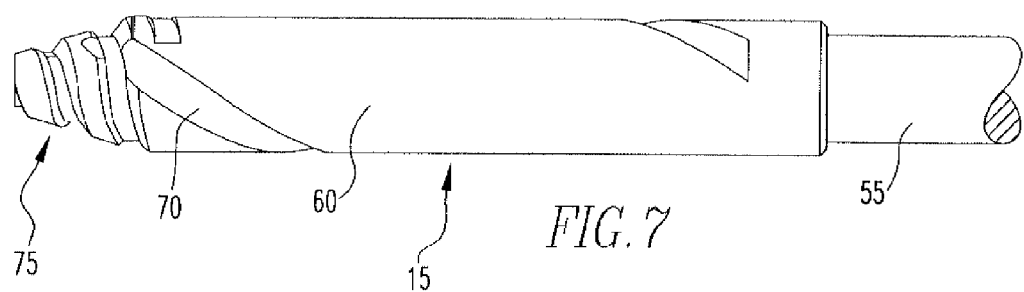
Figure 8:
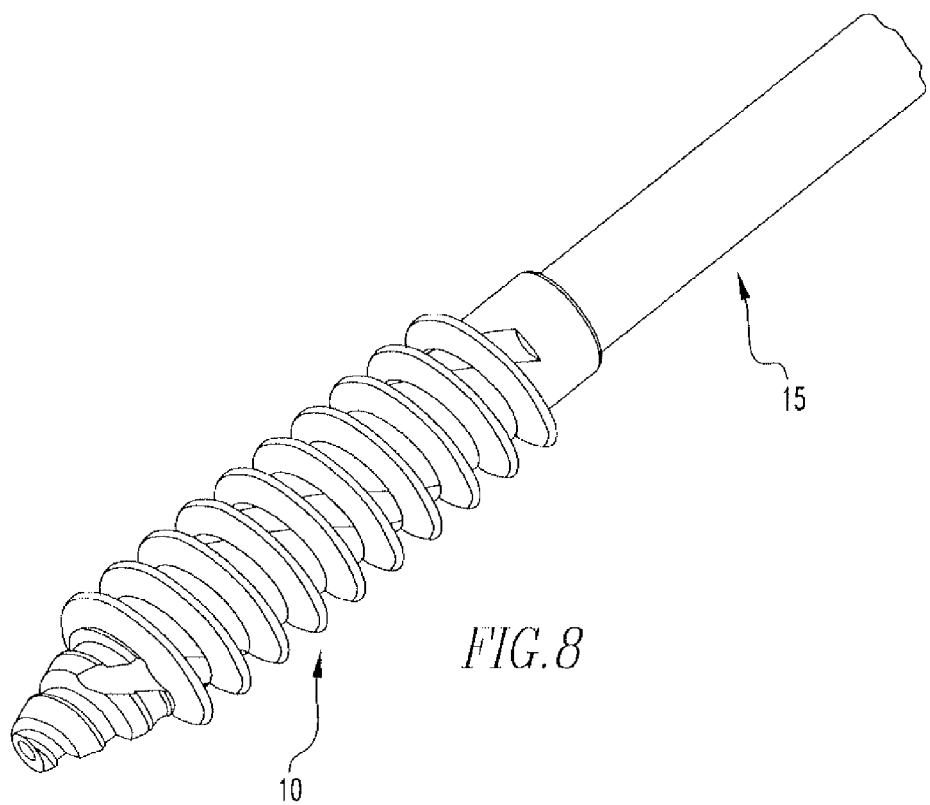
FIGS. 8-13 are schematic views showing a second helicoil interference fixation system formed in accordance with the present invention.
Figure 9:
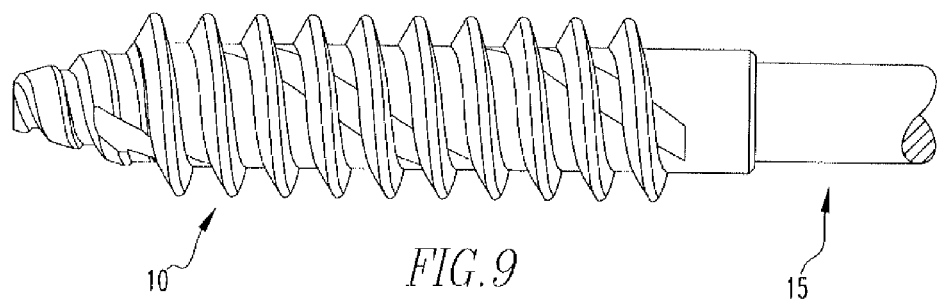
Figure 10:
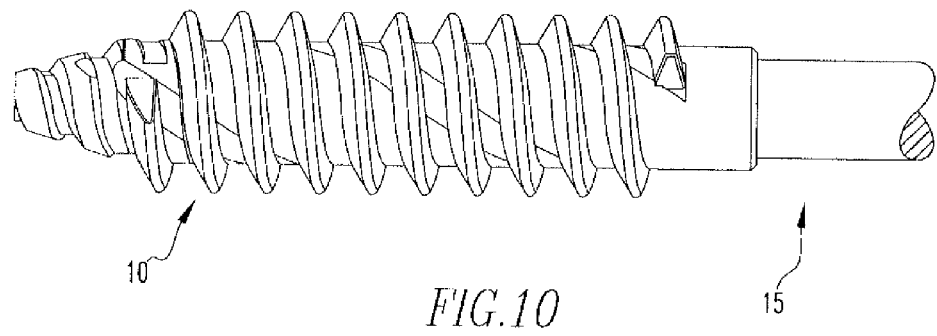

More particularly, and looking now at FIGS. 1-6, and particularly at FIG. 5, helicoil 10 generally comprises a helical body 20 terminating in a distal end 25 and a proximal end 30. Helical body 20 is constructed so that there are substantial spaces or gaps 35 between the turns 40 of the helical body. Spaces or gaps 35 facilitate bone-to-ligament in-growth, i.e., by providing large openings through the helical body. These large openings facilitate the flow of cell- and nutrient-bearing fluids through the helicoil, and permit the in-growth of tissue across the helicoil, so as to enhance bone-to-ligament in-growth.

One or more struts 45 are disposed within the interior of helical body 20, with the one or more struts 45 being secured to the interior surfaces 50 of helical body 20. The one or more struts 45 provide a means for turning helicoil 10 during deployment within the body, as will hereinafter be discussed in further detail. In addition, the one or more struts 45 can provide structural support for the turns 40 of helical body 20. The one or more struts 45 may be formed integral with helical body 20 (e.g., by a molding process), or they may be formed separately from helical body 20 and then attached to helical body 20 in a separate manufacturing process (e.g., by welding). Where the one or more struts 45 are formed integral with helical body 20, the one or more struts 45 can be used to help flow melt into position.

In one preferred form of the invention, the one or more struts 45 comprise helical structures. And in one particularly preferred form of the invention, the one or more struts 45 comprise helical structures which spiral in the opposite direction from the spiral of helical body 20, and the one or more struts 45 have a pitch which is substantially greater than the pitch of helical body 20. See FIG. 5.

Preferably, the number of struts 45, and their size, are selected so as to close off an insignificant portion of the spaces or gaps 35 between the turns 40 of helical body 20, whereby to substantially not impede the passage of fluids and tissue through the helicoil. At the same time, however, the number of struts 45, their size, and composition, are selected so as to provide an adequate means for turning helicoil 10 during deployment, and to provide any necessary support for the turns 40 of helical body 20.

In one preferred form of the present invention, one strut 45 is provided.

In another preferred form of the present invention, a plurality of struts 45 (e.g., two, three, four or more struts) are provided.

And in one preferred form of the present invention, the struts 45 collectively close off less than fifty percent (50%) of the spaces or gaps 35 between the turns 40 of helical body 20.

And in one particularly preferred form of the present invention, the struts 45 collectively close off less than twenty percent (20%) of the spaces or gaps 35 between the turns 40 of helical body 20.

Helicoil 10 is formed out of one or more biocompatible materials. These biocompatible materials may be non-absorbable (e.g., stainless steel or plastic) or absorbable (e.g., a bioabsorbable polymer). In one preferred form of the present invention, helicoil 10 preferably comprises a bioabsorbable polymer such as polylactic acid (PLA), polyglycolic acid (PGA), etc. In any case, however, helicoil 10 comprises a material which is capable of providing the strength needed to set the fixation device into position and to hold the graft ligament in position while bone-to-ligament in-growth occurs.

Inserter 15 is shown in FIGS. 1-4 and 7. Inserter 15 generally comprises a shaft 55 having a distal end 60 and a proximal end 65. One or more grooves 70 are formed on the distal end of shaft 55. Grooves 70 receive the one or more struts 45 of helicoil 10, in order that helicoil 10 may be mounted on the distal end of shaft 55 and rotated by rotation of shaft 55. A tapered seat-forming thread 75 (e.g., a tapered cutting thread, a tapered opening or dilating thread, etc.) is formed in shaft 55 distal to grooves 70. Tapered seat-forming thread 75 serves to precede helicoil 10 into the space between the graft ligament and the wall of the bone tunnel, and then to form a lead-in or opening in the graft ligament and the wall of the bone tunnel for receiving the turns 40 of helical body 20, in much the same manner as a tap that creates the thread form, as will hereinafter be discussed in further detail. A handle 80 is mounted on the proximal end of shaft 55 in order to facilitate rotation of shaft 55 by the surgeon.

It should be appreciated that tapered seat-forming thread 75 is matched to helicoil 10 so that when helicoil 10 is mounted on inserter 15, tapered seat-forming thread 75 provides the proper lead-in for helicoil 10.

Preferably, interior surfaces 50 of helical body 20 and distal end 60 of inserter 15 are tapered, expanding outwardly in the proximal direction, so that helicoil 10 and inserter 15 form a positive seat such that the interior surface of the helicoil is in direct contact with the tapered body diameter of the inserter.

Thus it will be seen that, when helicoil 10 is mounted on the distal end of shaft 55, inserter 15 may be used to advance the helicoil to a surgical site and, via rotation of handle 80, turn helicoil 10 into the gap between a graft ligament and the wall of a bone tunnel, whereby to create an interference fixation of the graft ligament in the bone tunnel. Significantly, inasmuch as inserter 15 has a tapered seat-forming thread 75 formed on its distal end in advance of helicoil 10, the tapered seat-forming thread can form a seat into the tissue in advance of helicoil 10, whereby to permit the helicoil to advance easily into the tissue and create the desired interference fixation. Accordingly, helicoil 10 does not need to have any penetrating point on its distal end in order to penetrate the tissue.

If desired, inserter 15 may be cannulated so that the inserter and helicoil 10 may be deployed over a guidewire, as will hereinafter be discussed.

FIGS. 8-13 show another helicoil interference fixation system 5, wherein helicoil 10 comprises two struts 45 and inserter 15 comprises two grooves 70. The use of two struts 45, rather than one strut 45, may be advantageous since it may distribute the load imposed during rotation over a larger surface area. This may be important where helicoil 10 is formed out of a bioabsorbable polymer.

Helicoil interference fixation system 5 may be utilized in a manner generally similar to that of a conventional interference screw system in order to attach a graft ligament to a bone.

More particularly, and looking now at FIGS. 14-25, there are shown various aspects of an ACL reconstruction effected using helicoil interference fixation system 5.

Figure 14:
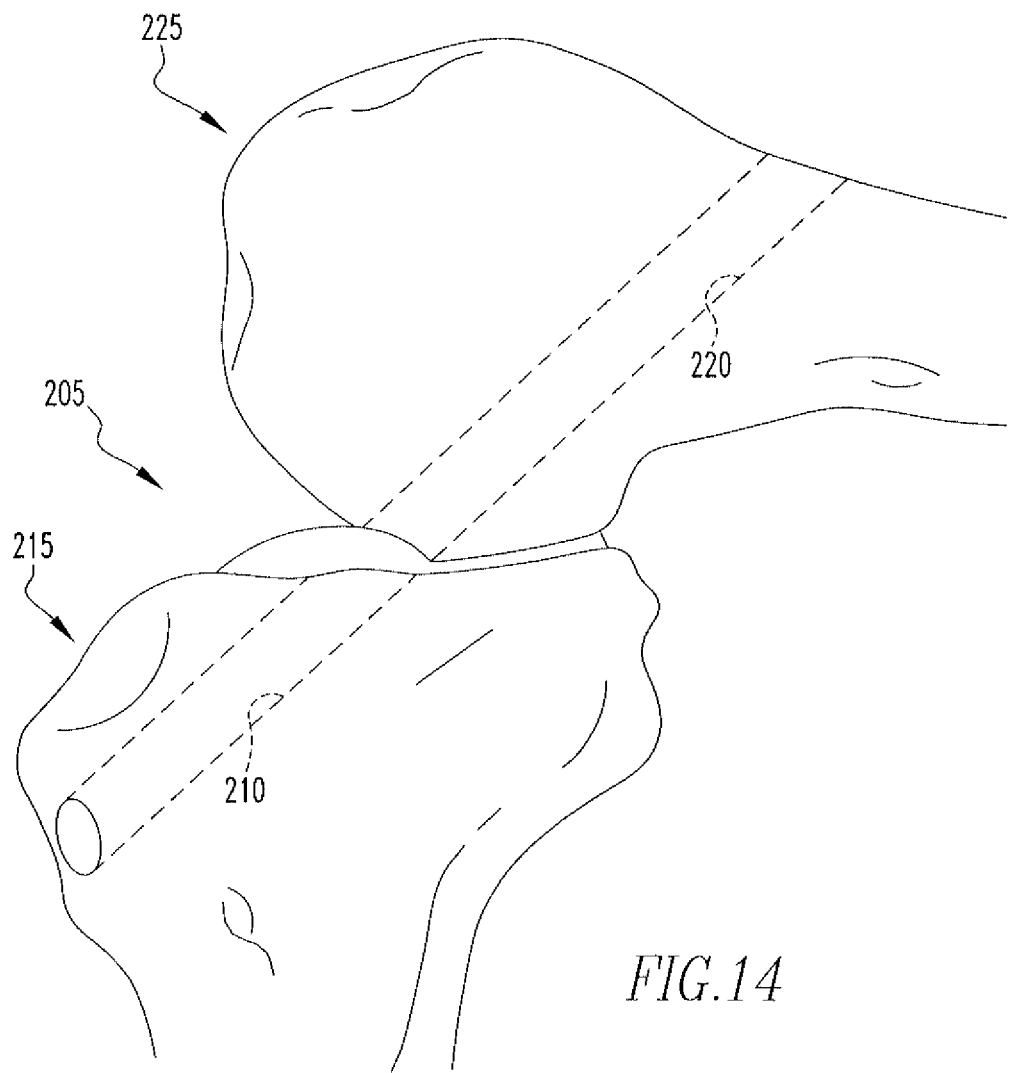
FIGS. 14-20 are schematic views showing a femoral fixation using the second helicoil interference fixation system of FIGS. 8-13.

FIG. 14 shows a typical knee joint 205, with the joint having been prepared for an ACL reconstruction, i.e., with the natural ACL having been removed, and with a tibial bone tunnel 210 having been formed in tibia 215, and with a femoral bone tunnel 220 having been formed in femur 225.

Figure 15:
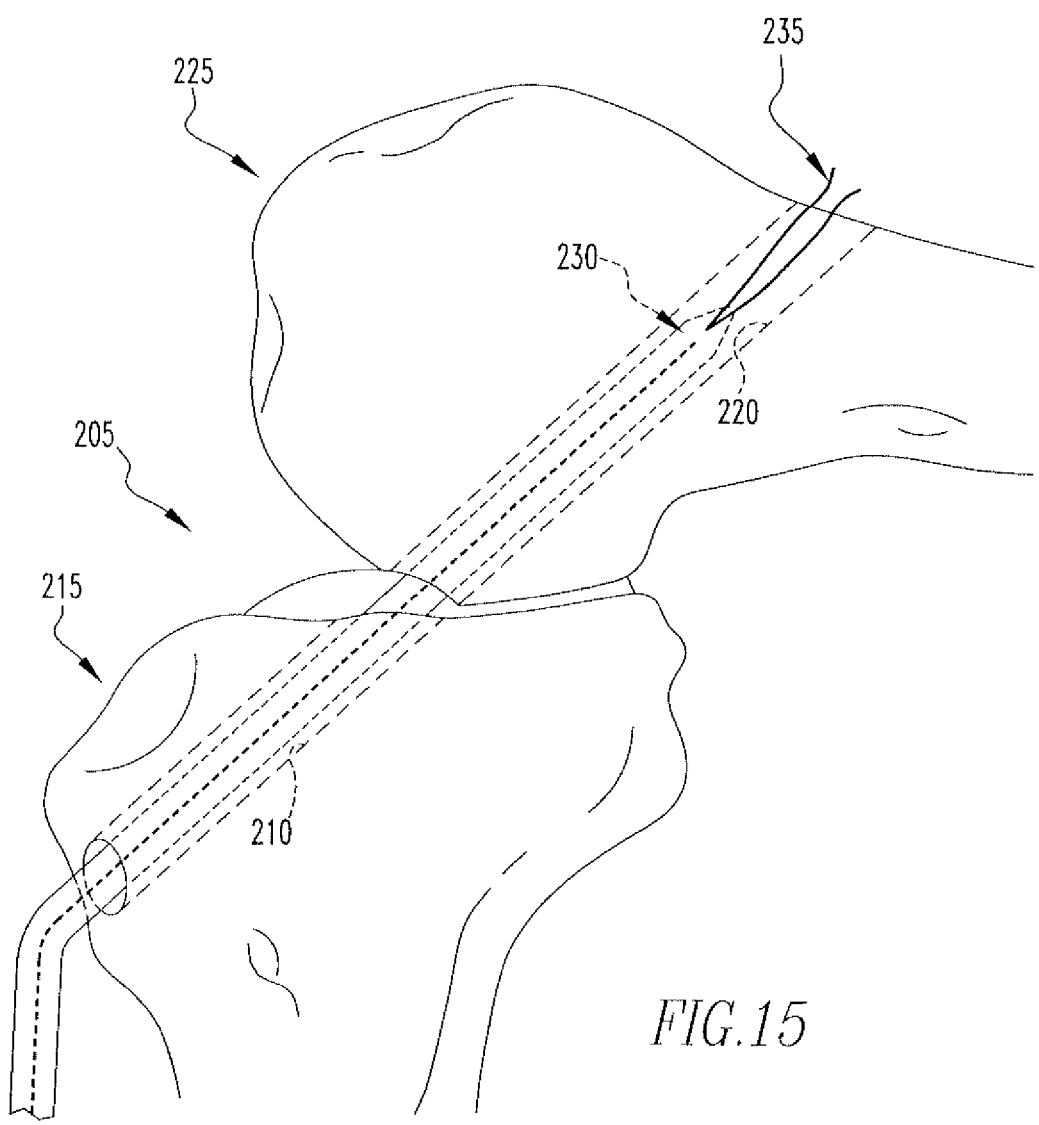

FIG. 15 is a view similar to that of FIG. 14, except that a graft ligament 230 has been positioned in femoral bone tunnel 220 and tibial bone tunnel 210 in accordance with ways well known in the art. By way of example, graft ligament 230 may be "towed" up through tibial bone tunnel 210 and into femoral bone tunnel 220 using a tow suture 235.

Figure 16:
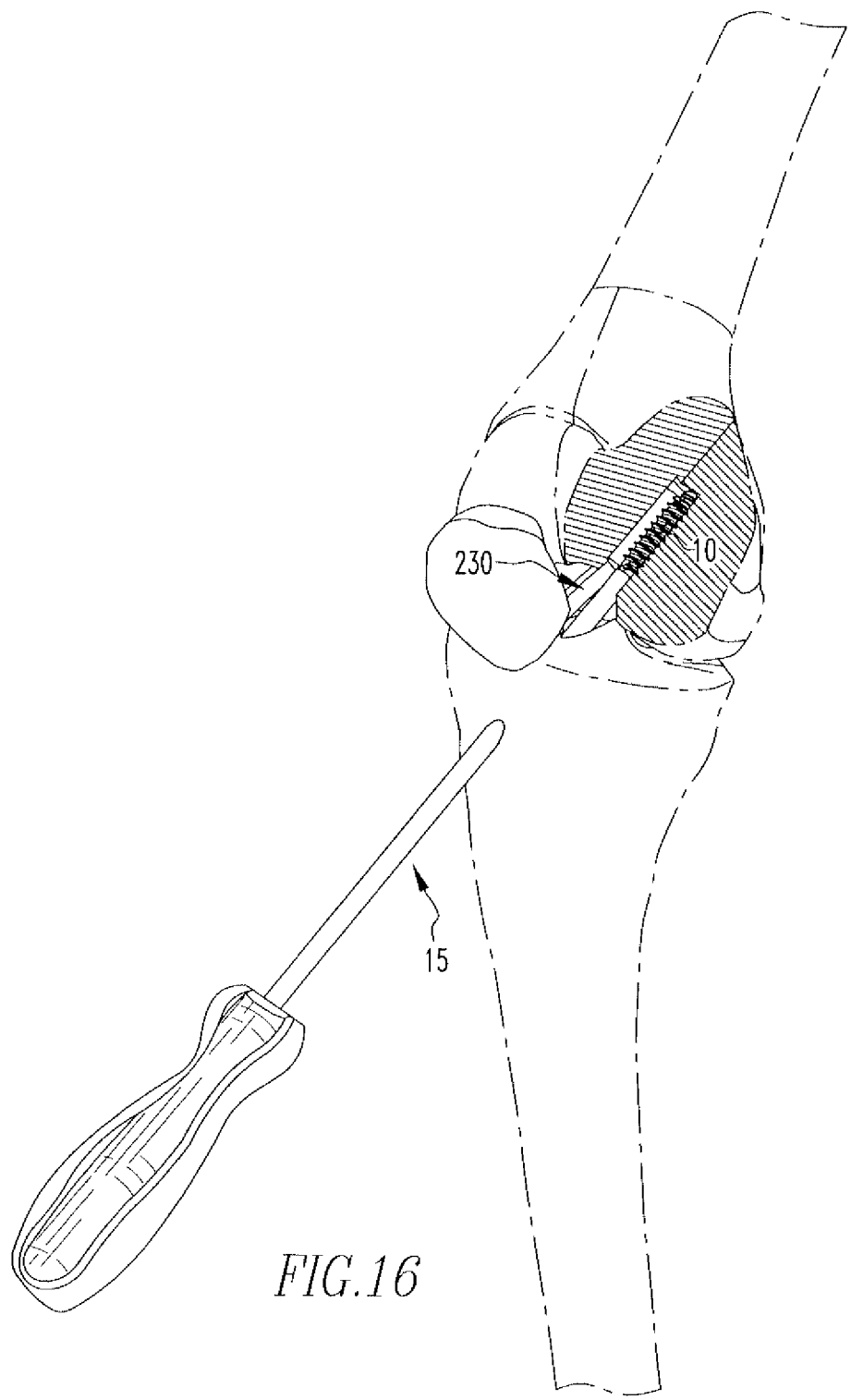
Figure 17:
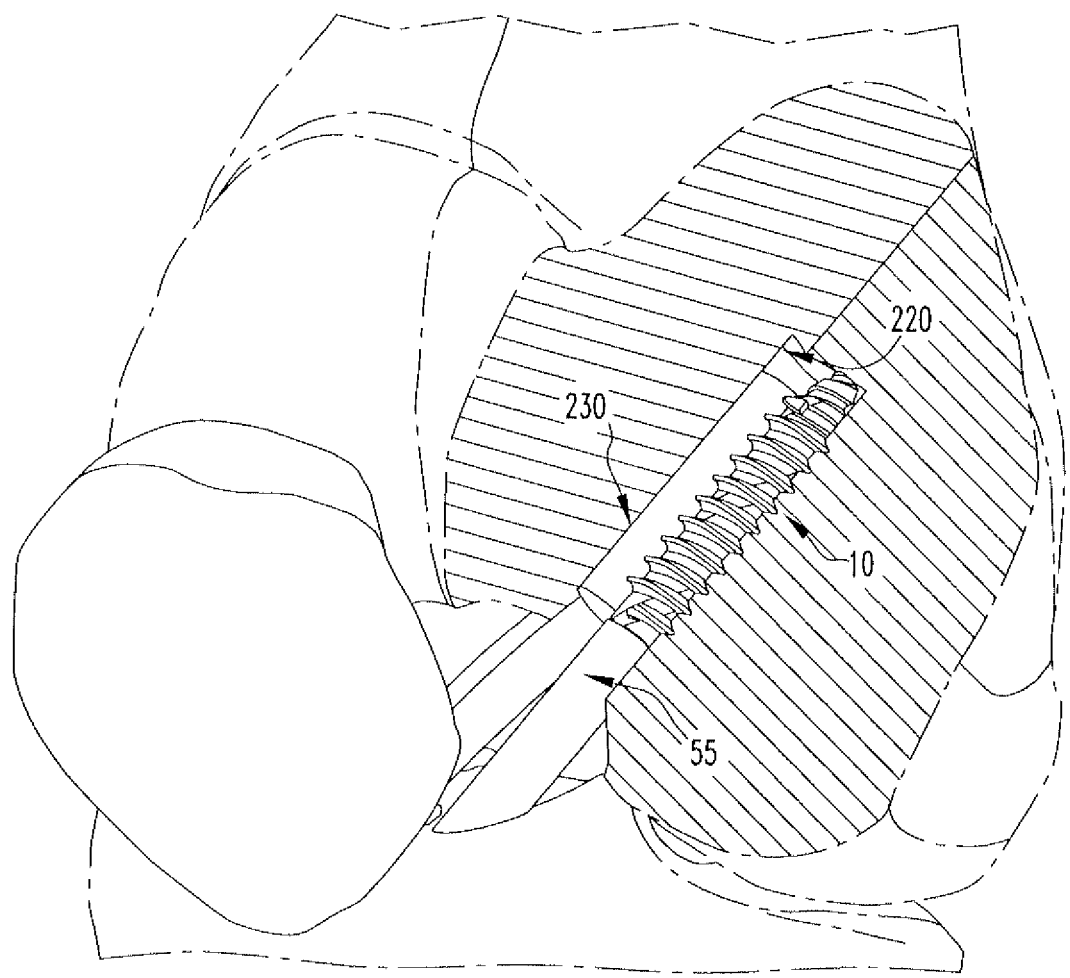

FIGS. 16 and 17 show graft ligament 230 being made fast in femoral tunnel 220 using helicoil interference fixation system 5. More particularly, in accordance with the present invention, helicoil 10 is mounted on the distal end of inserter 15 by fitting the struts 45 of helicoil 10 into the grooves 70 of the inserter. Then the inserter is used to advance helicoil 10 through tibial tunnel 210, across the interior of knee joint 205, and up into the femoral tunnel 220. If desired, inserter 15 may be cannulated, so that the inserter and helicoil are advanced over a guidewire of the sort well known in the art. As the distal tip of the inserter is advanced, the tapered seat-forming thread 75 first finds its way into the space between the graft ligament 230 and the side wall of femoral bone tunnel 220. Then, as the inserter is turned, tapered seat-forming thread 75 forms a seat into the tissue in advance of helicoil 10, and helicoil 10 is advanced into the tissue so that the turns of helical body 20 seat themselves in the seat formed by seat-forming thread 75. As this occurs, the graft ligament is driven laterally, into engagement with the opposing side wall of the bone tunnel. This action sets helicoil 10 between the side wall of femoral bone tunnel 220 and graft ligament 230, thereby securing the interference fit between graft ligament 230 and the side wall of the bone tunnel, whereby to secure graft ligament 230 to the bone.

Figure 18:
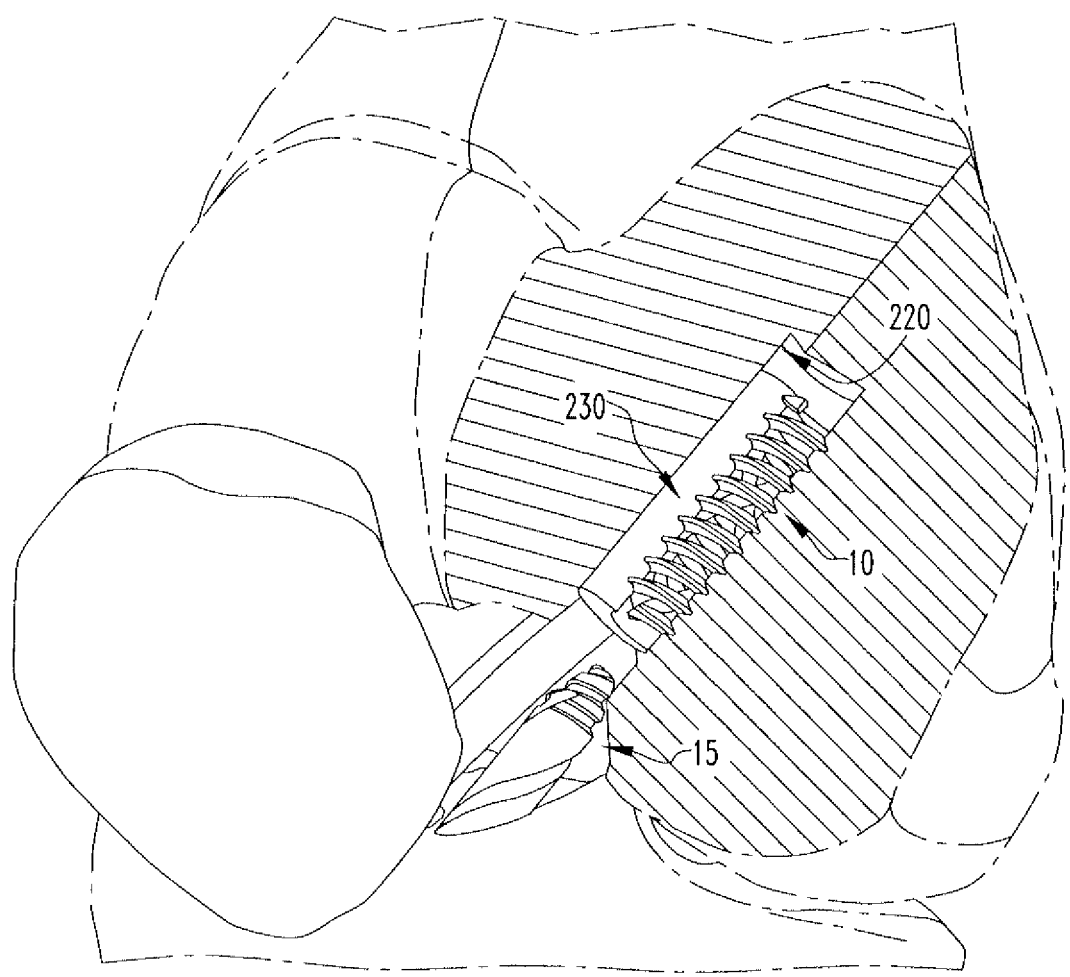
Figure 19:
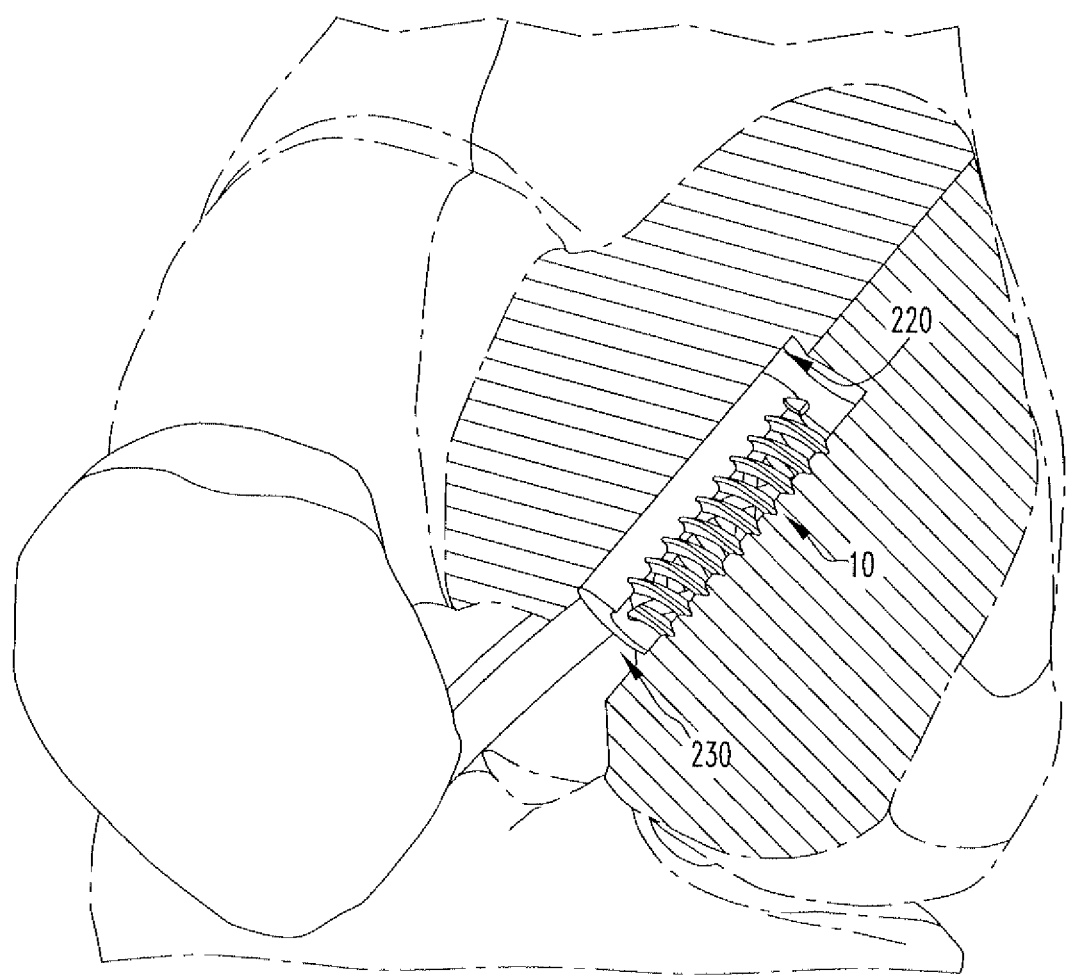
Figure 20:
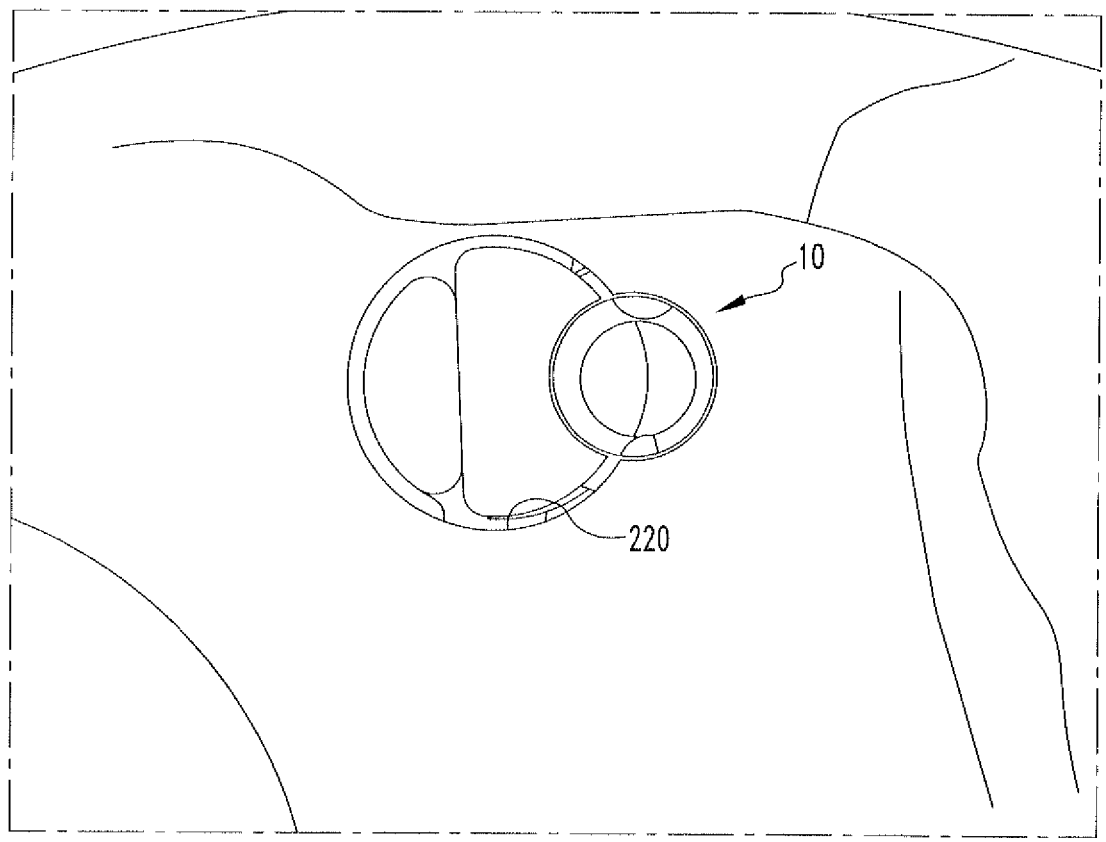
Figure 21:
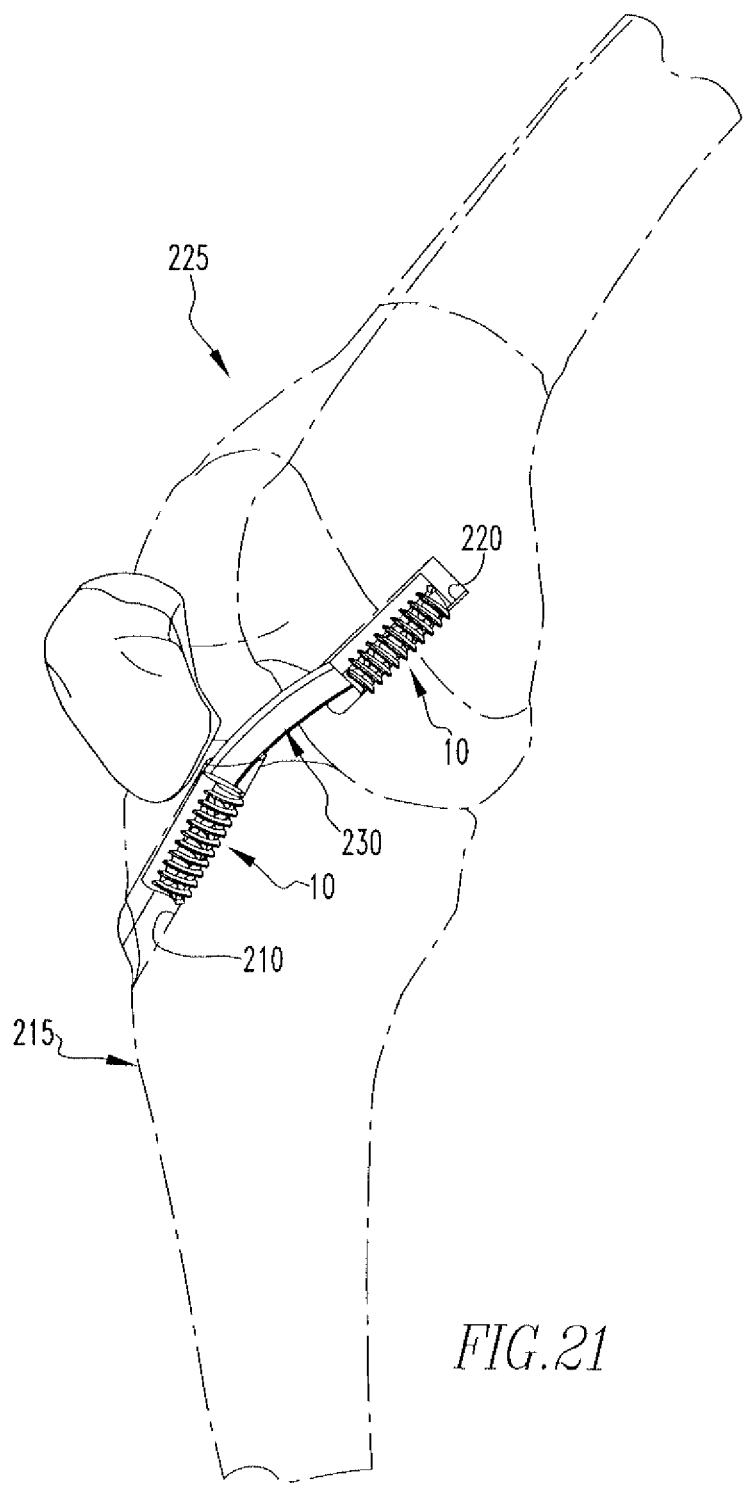
FIGS. 21-25 are schematic views showing a full ACL reconstruction using the second helicoil interference fixation system of FIGS. 8-13.
Figure 22:
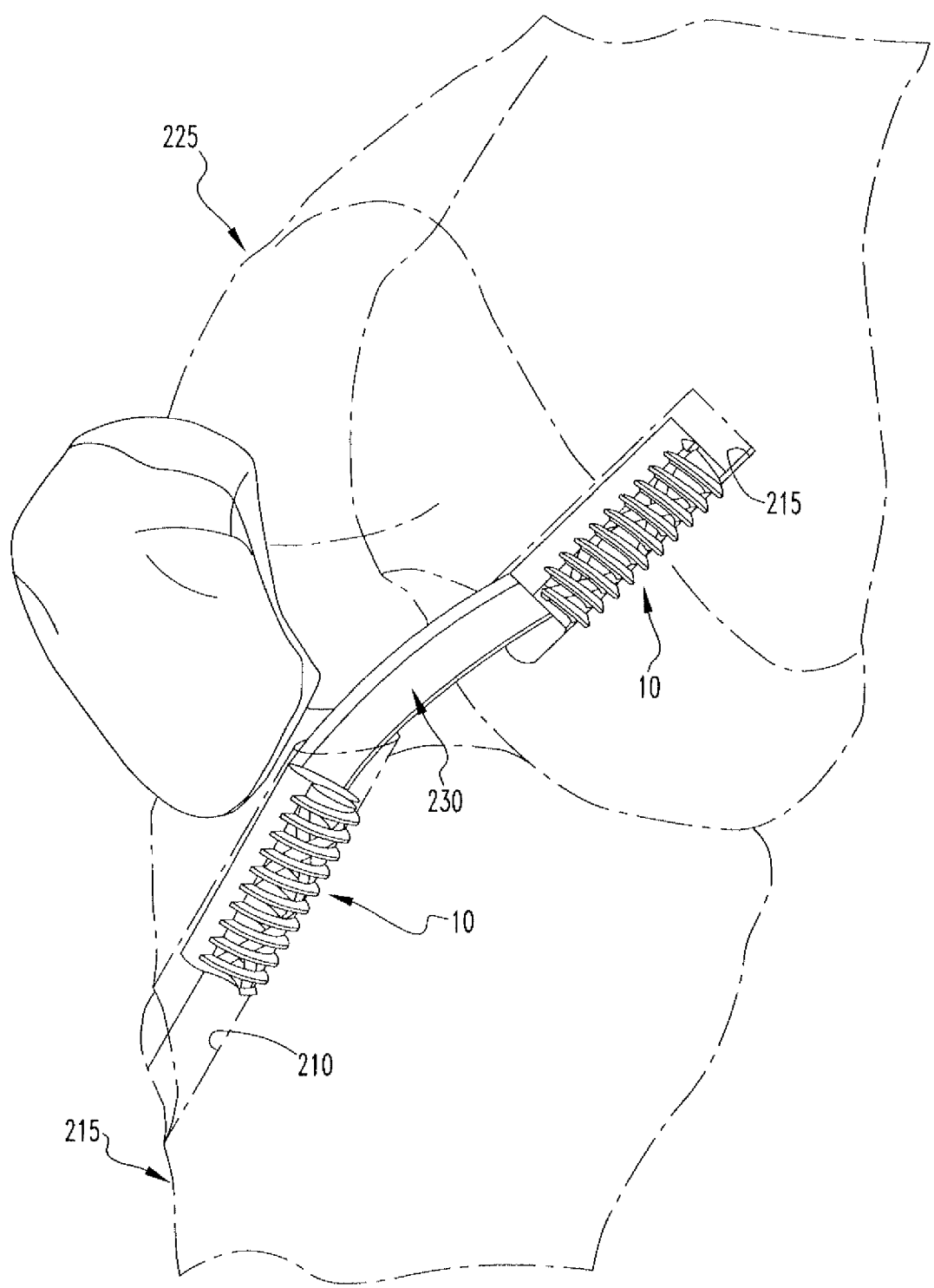
Figure 23:
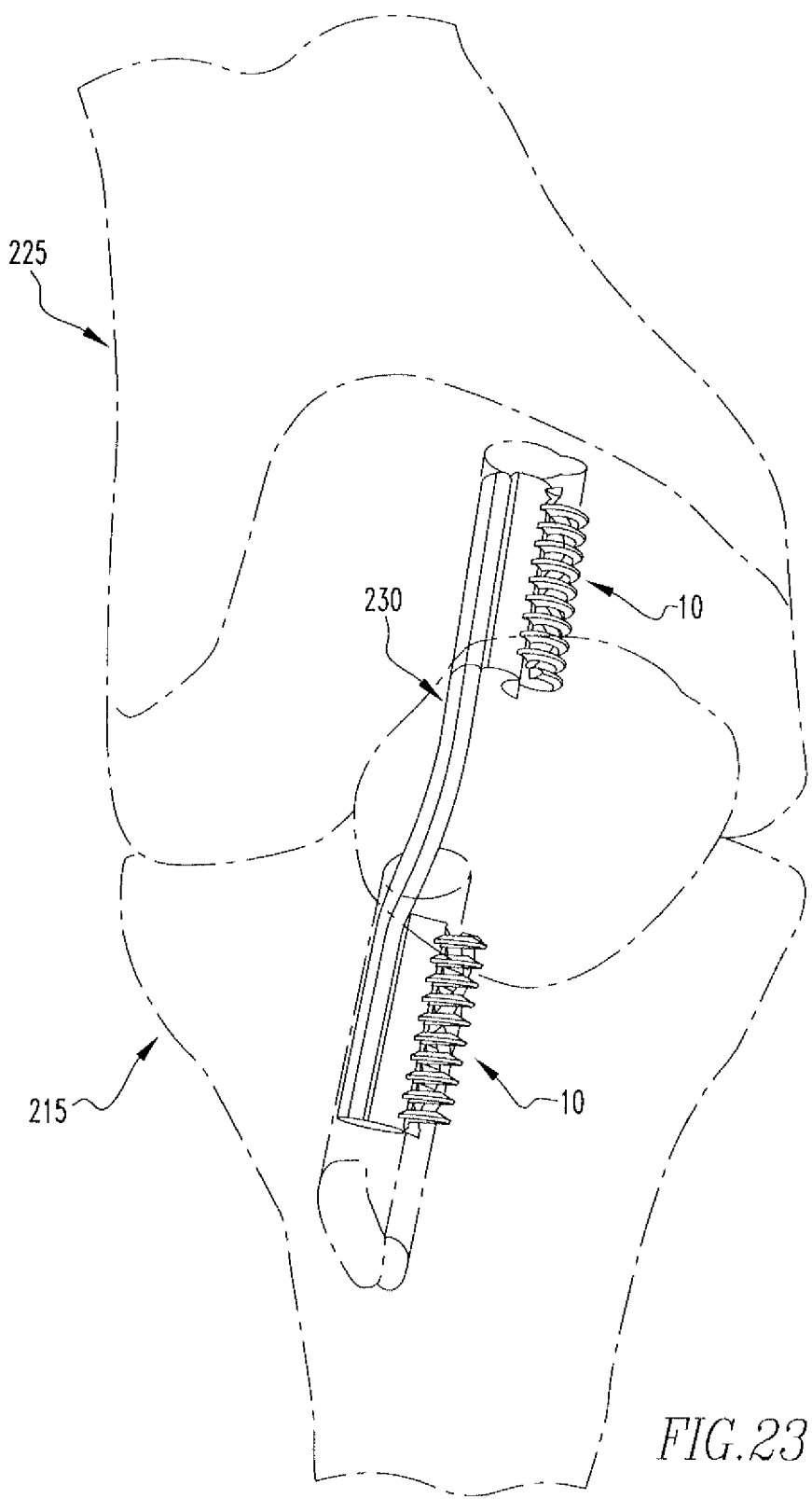
Figure 24:
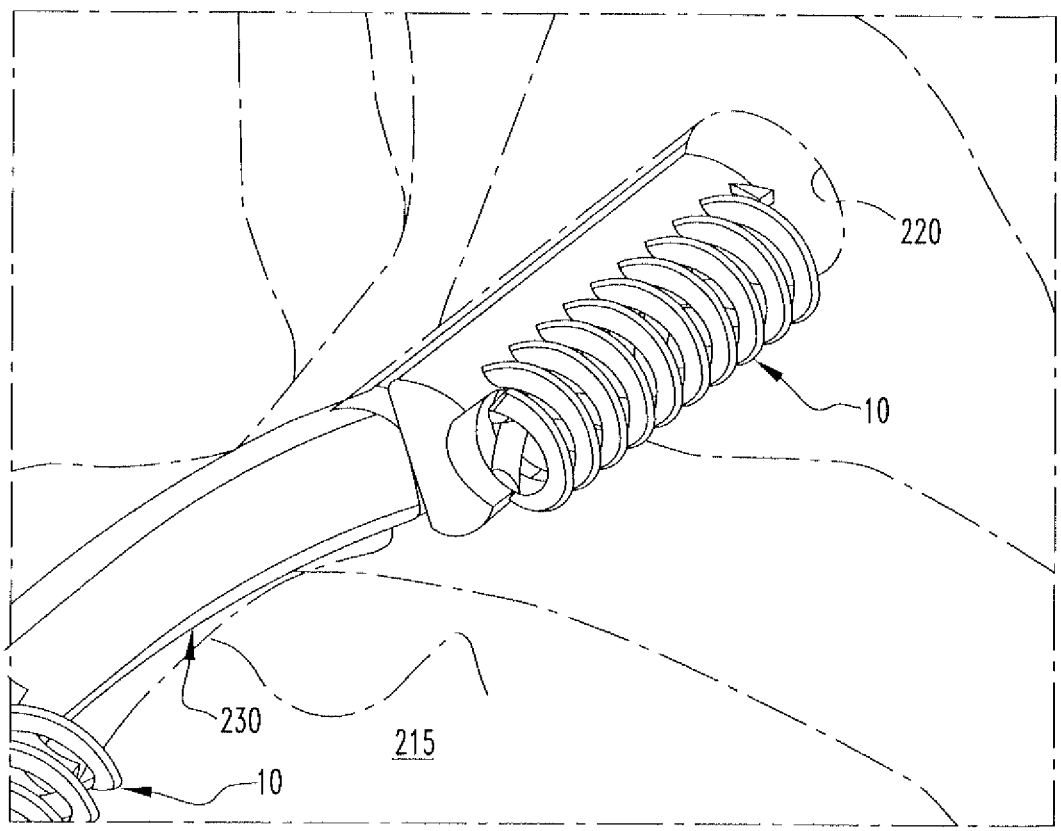
Figure 25:
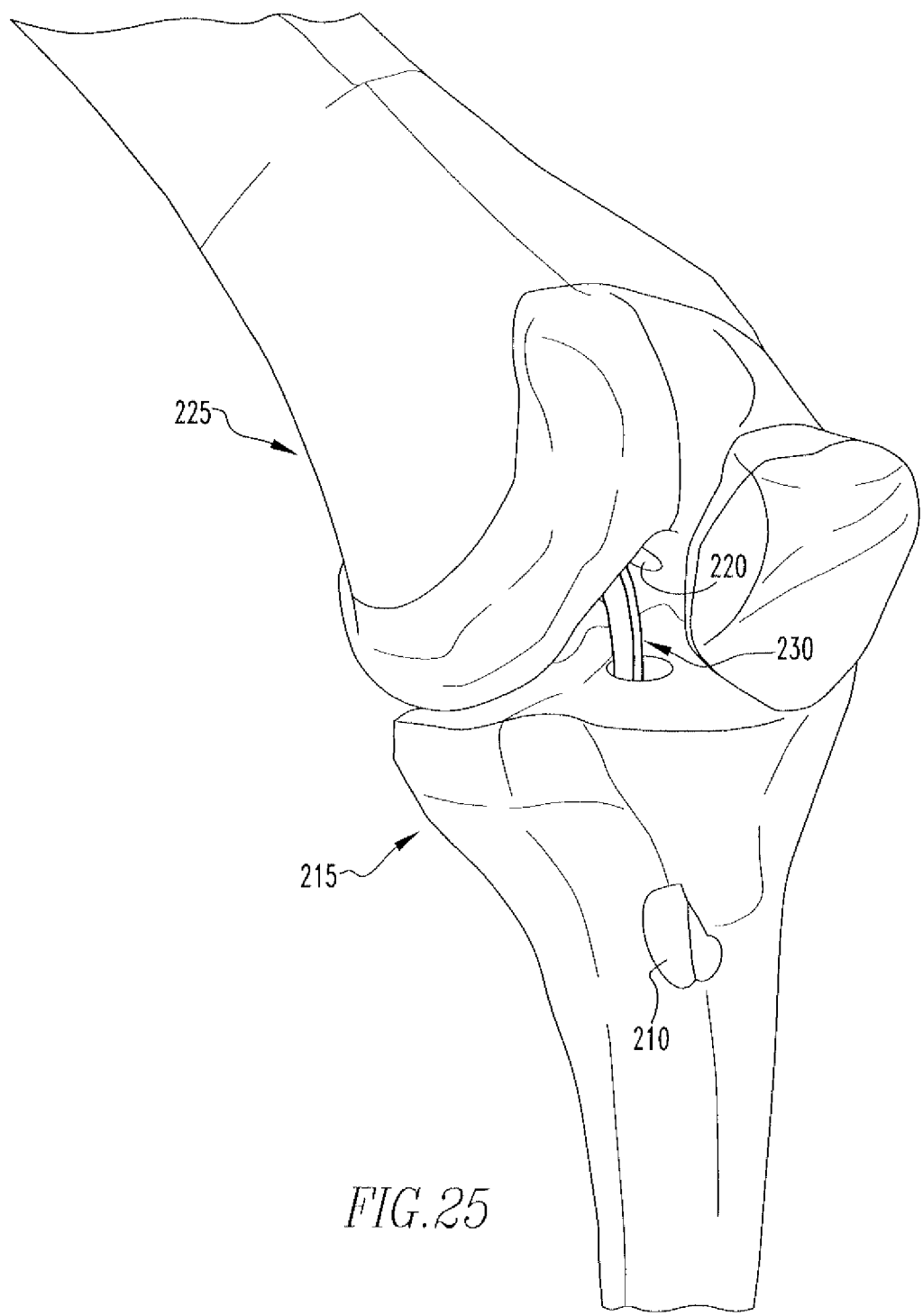

Thereafter, and looking now at FIGS. 18 and 19, inserter 15 is withdrawn, leaving helicoil 10 lodged in position between the graft ligament and the side wall of the bone tunnel. As seen in FIG. 20, helicoil 10 maintains the interference fit established between graft ligament 220 and the side wall of the bone tunnel, thereby securing the graft ligament to the bone.

If desired, helicoil interference fixation system 5 can then be used in a similar manner to form a tibial fixation. See FIGS. 21-25.

Significantly, forming the fixation device in the form of an open helical coil has proven particularly advantageous, inasmuch as the open helical coil provides the strength needed to set the fixation device into position, and hold the graft ligament in position while bone-to-ligament in-growth occurs, while still providing extraordinary access through the body of the fixation device. Thus, cell- and nutrient-bearing fluids can move substantially unimpeded through the body of helicoil 10, and tissue in-growth can occur across the body of helicoil 10.

Furthermore, it has been found that when the graft ligament thereafter imposes axial loads on the interference fit, struts 45 help maintain the structural integrity of turns 40 of helical body 20, whereby to ensure the integrity of the interference fit.

Figure 26:
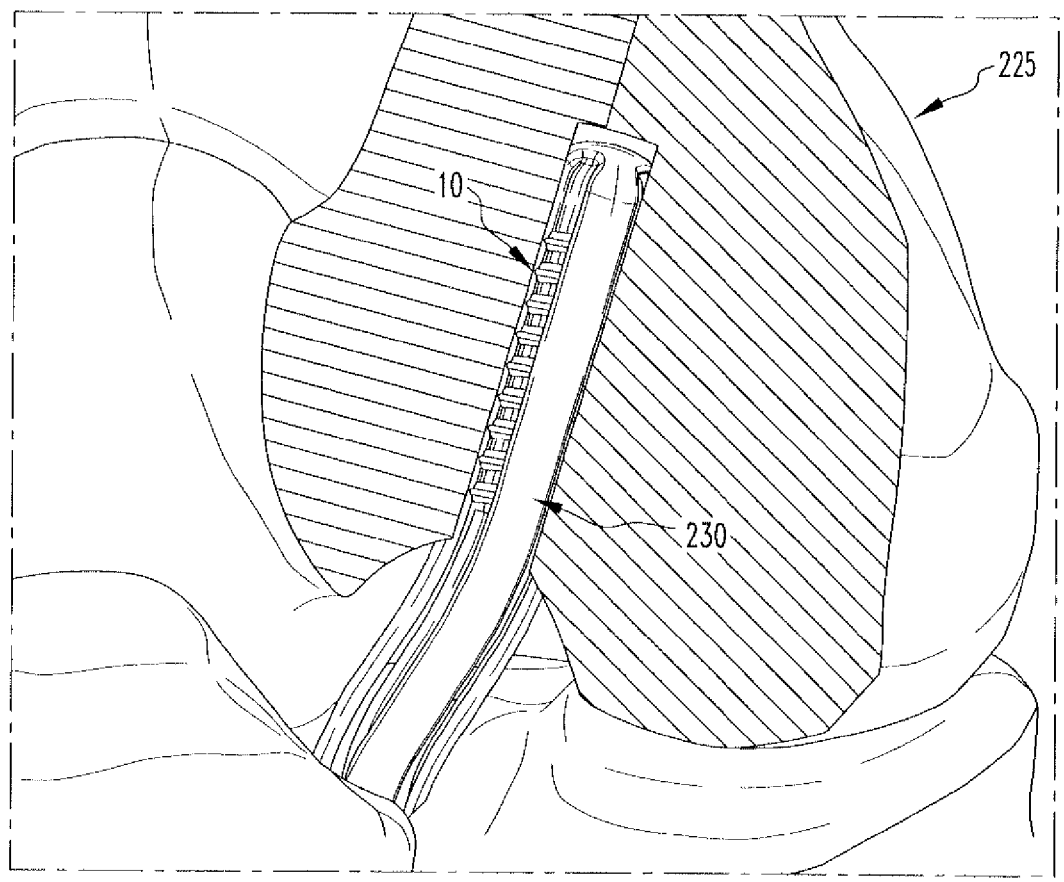
FIGS. 26-28 are schematic views showing a soft tissue ACL fixation using the second helicoil interference fixation system of FIGS. 8-13.
Figure 27:
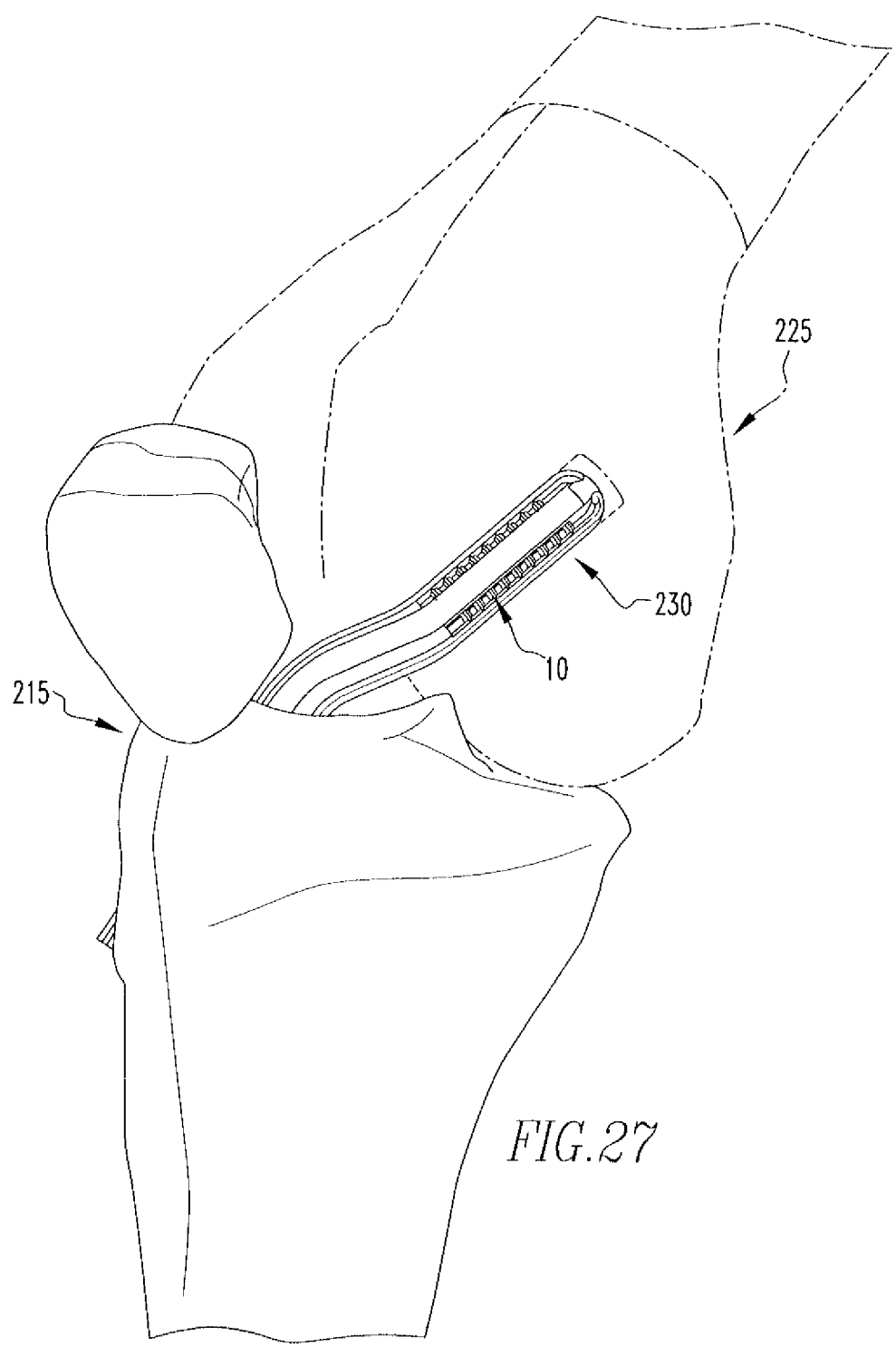
Figure 28:
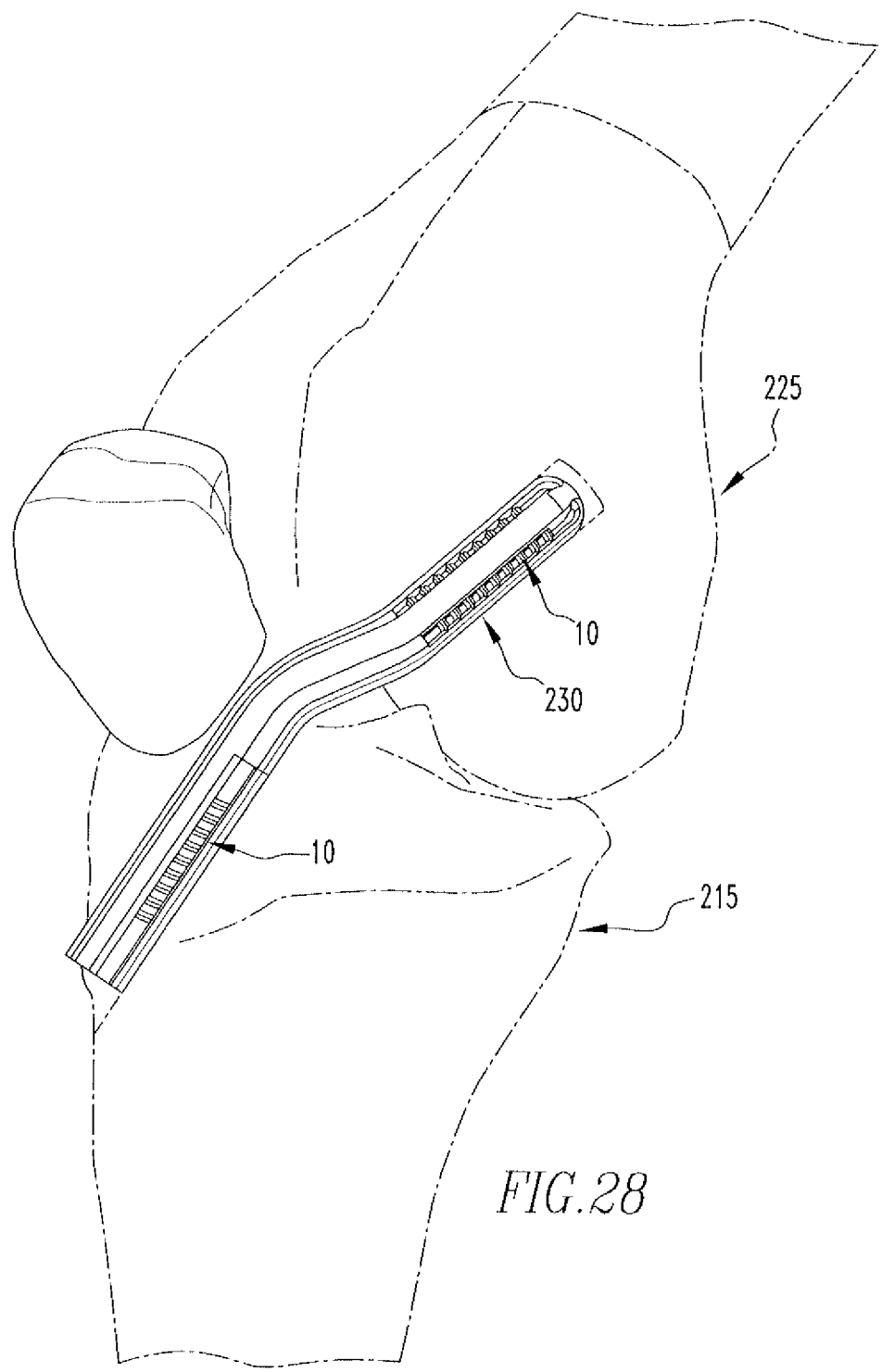

In FIGS. 16-24, graft ligament 230 is shown to include bone blocks at the ends of the ligament, e.g., graft ligament 10 may be a patella tendon with bone blocks attached. However, as seen in FIGS. 26-28, graft ligament 230 can also constitute only soft tissue, e.g., graft ligament 230 may comprise a semitendinosus tendon and/or a gracilis tendon, and/or a synthetic device.

Figure 11:
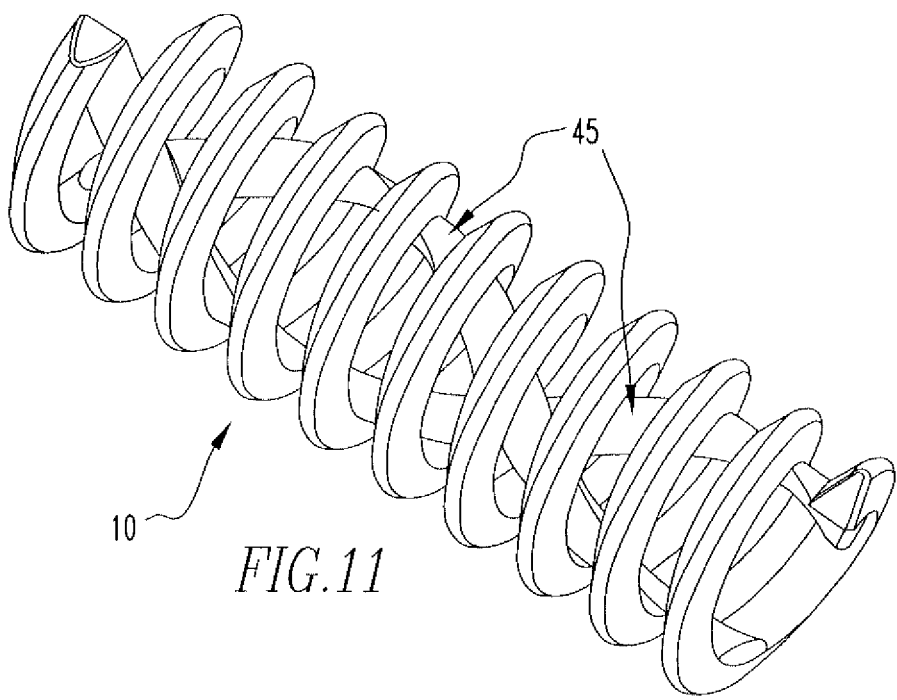
Figure 12:
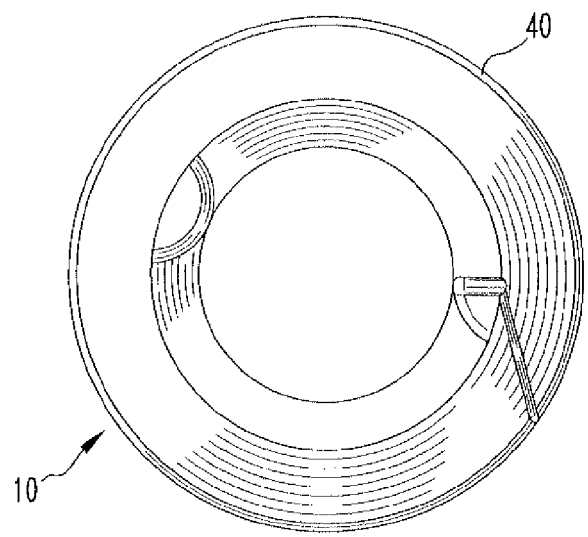
Figure 13:
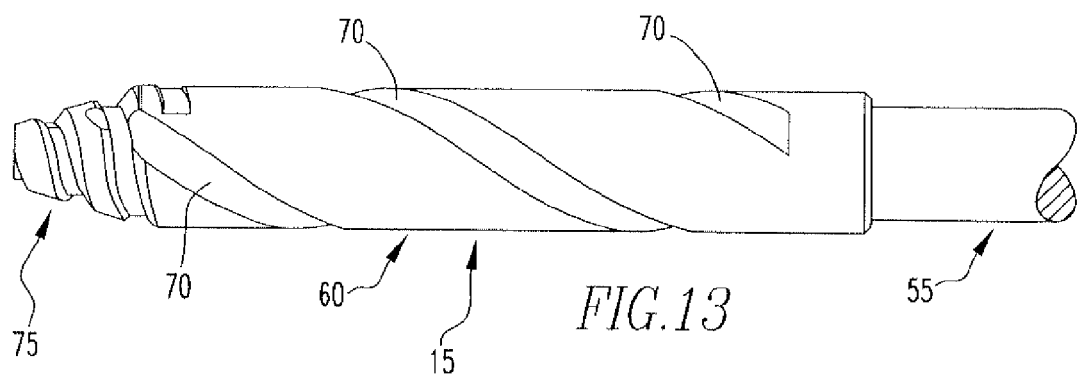
Figure 29:
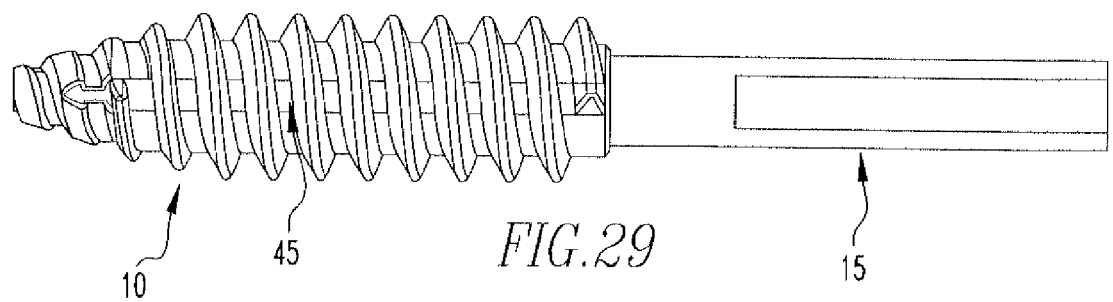
FIGS. 29-31 are schematic views showing a third helicoil interference fixation system formed in accordance with the present invention.
Figure 30:
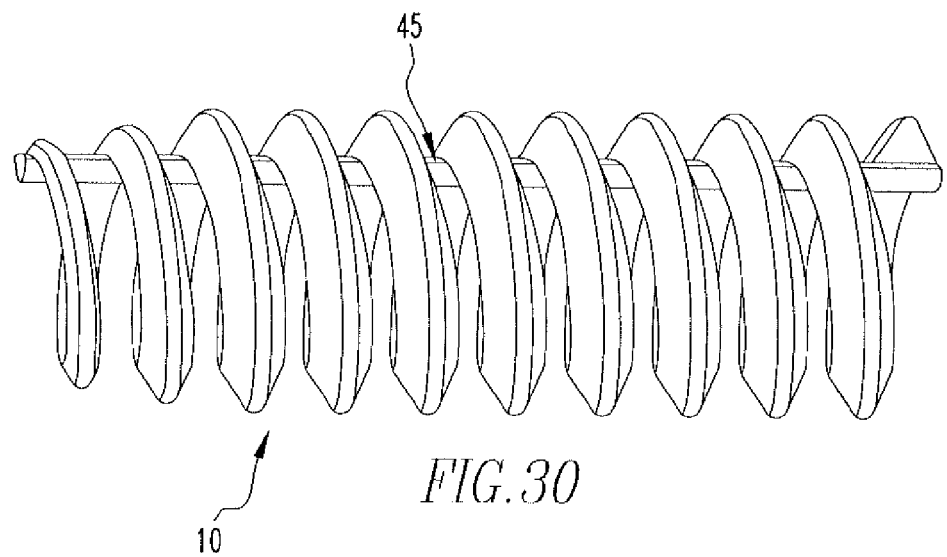
Figure 31:
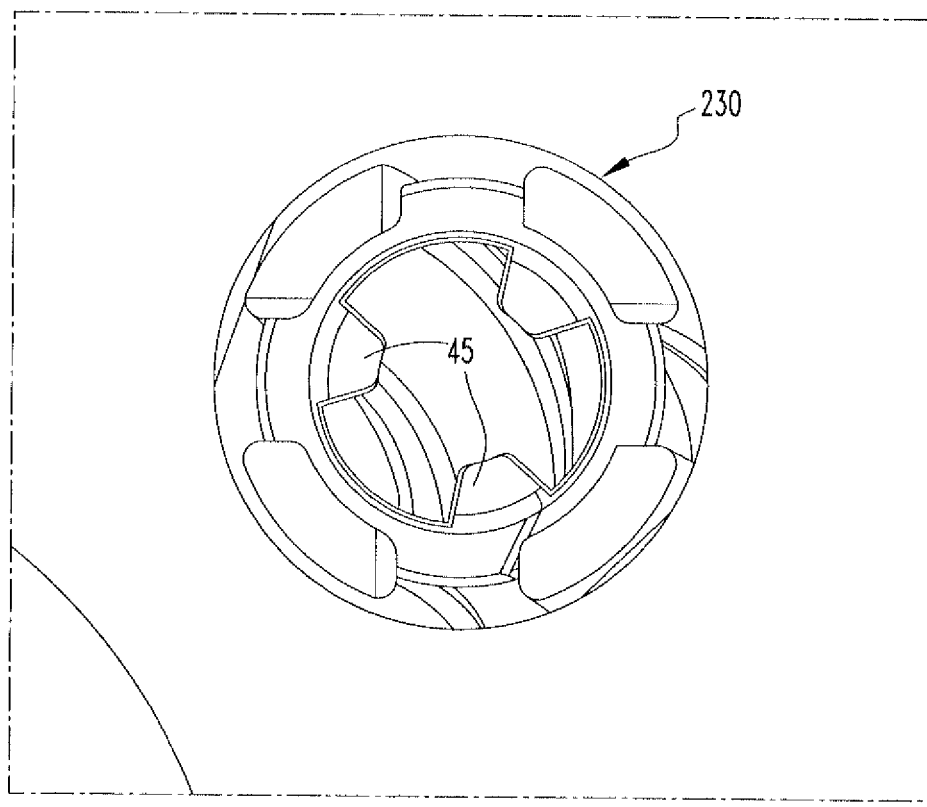

In FIGS. 5 and 11, the one or more struts 45 are shown as having a helical structure. However, the one or more struts 45 may also be formed with a straight configuration. See, for example, FIGS. 29-30, which show a helicoil 10 with a single straight strut 45, and FIG. 31 which shows a helicoil 10 with multiple straight struts 45.

Figure 32:
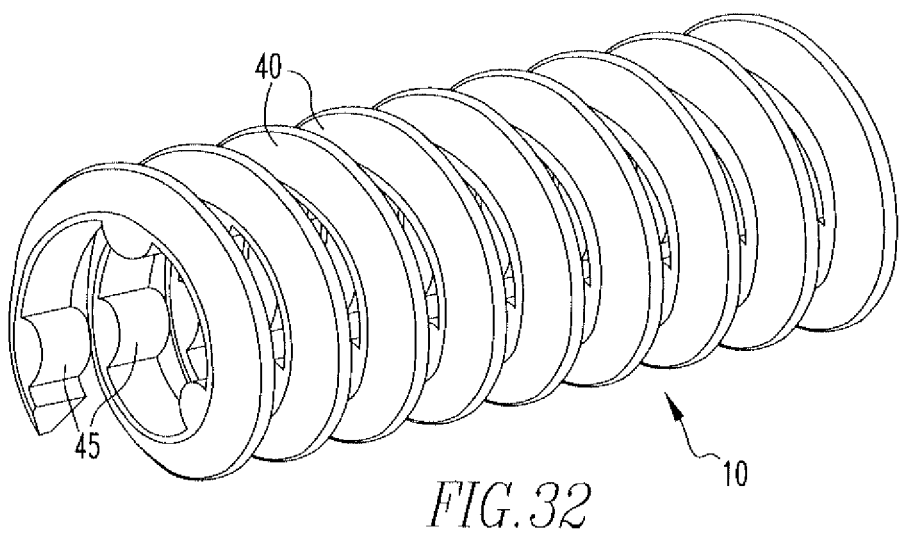
FIG. 32 is schematic view showing a fourth helicoil interference fixation system formed in accordance with the present invention.
Figure 33:
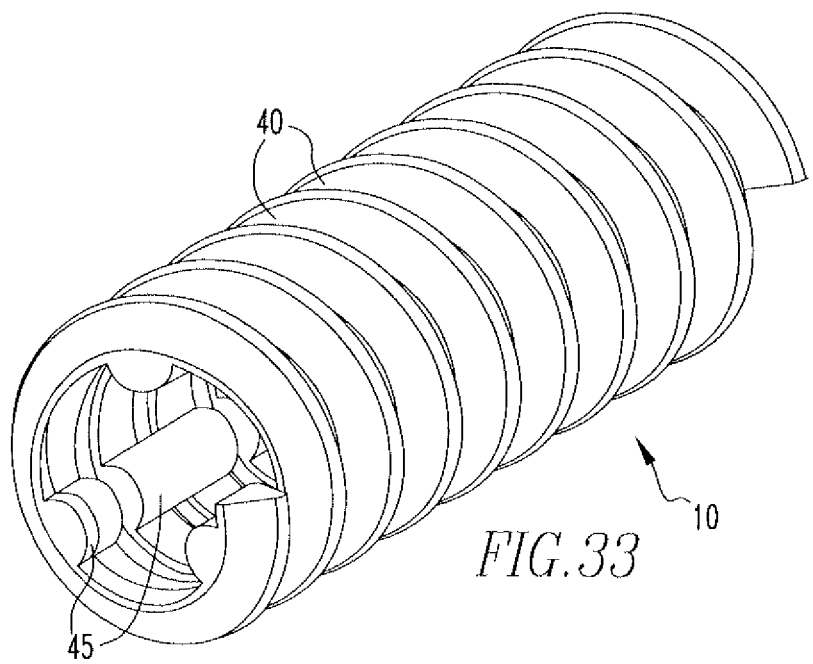
FIG. 33 is a schematic view showing a fifth helicoil interference fixation system formed in accordance with the present invention.

Furthermore, as seen in FIG. 32, the one or more struts 45 may be interrupted between turns 40 or, as seen in FIG. 33, the one or more struts 45 may be selectively interrupted between turns 40.

Figure 34:
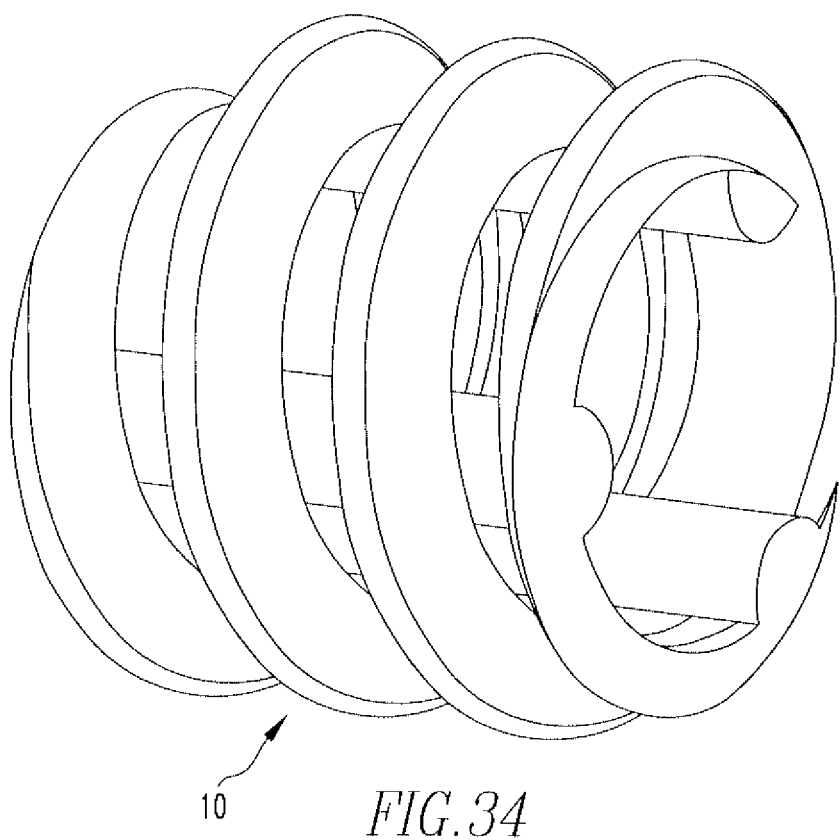
FIGS. 34-36 are schematic views showing a sixth helicoil interference fixation system formed in accordance with the present invention.
Figure 35:
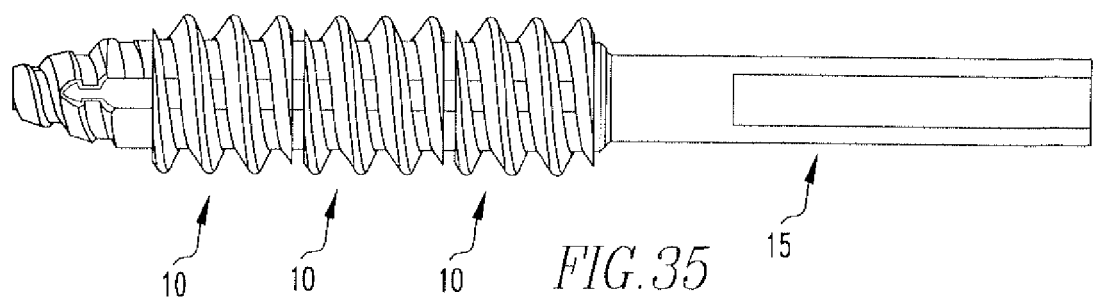
Figure 36:
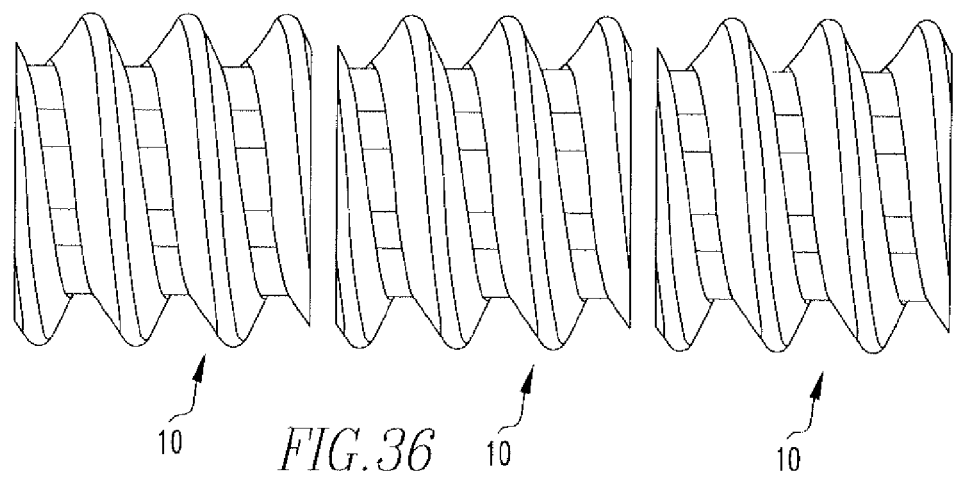

It should also be appreciated that an interference fit may be formed using a plurality of helicoils 10. Thus, as seen in FIGS. 34-36, a plurality of helicoils 10 may be loaded on an inserter 15 and used for a collective interference fit.

Figure 37:
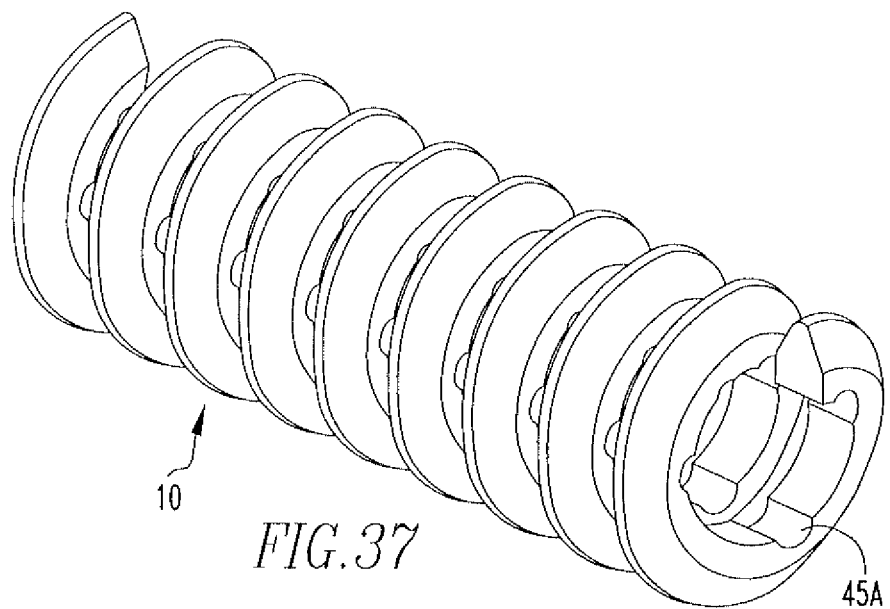
FIG. 37 is a schematic view showing a seventh helicoil interference fixation system formed in accordance with the present invention.

If desired, and looking now at FIG. 37, the one or more struts 45 may be replaced with recesses 45A. In this case, grooves 70 on inserter 15 are replaced by corresponding ribs (not shown), whereby to permit inserter 15 to rotatably drive helicoil 10.

Figure 38:
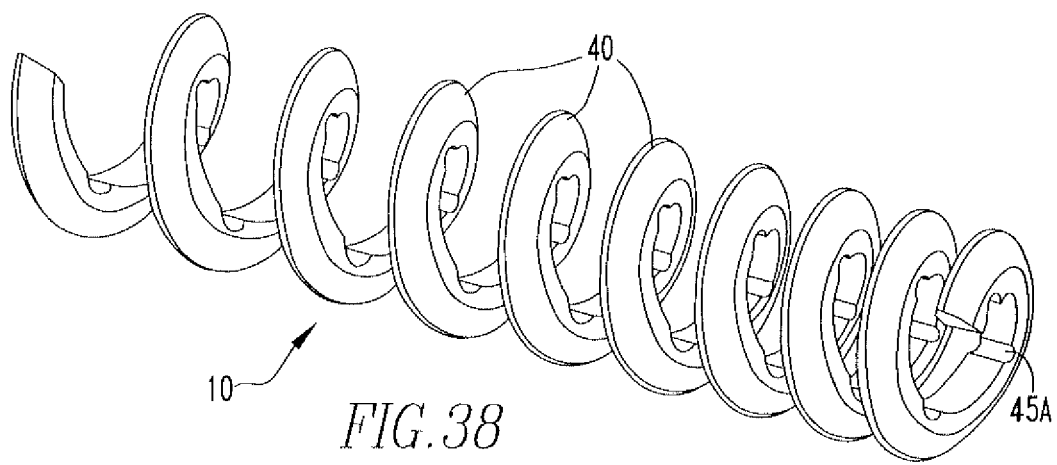
FIG. 38 is a schematic view showing an eighth helicoil interference fixation system formed in accordance with the present invention.
Figure 39:
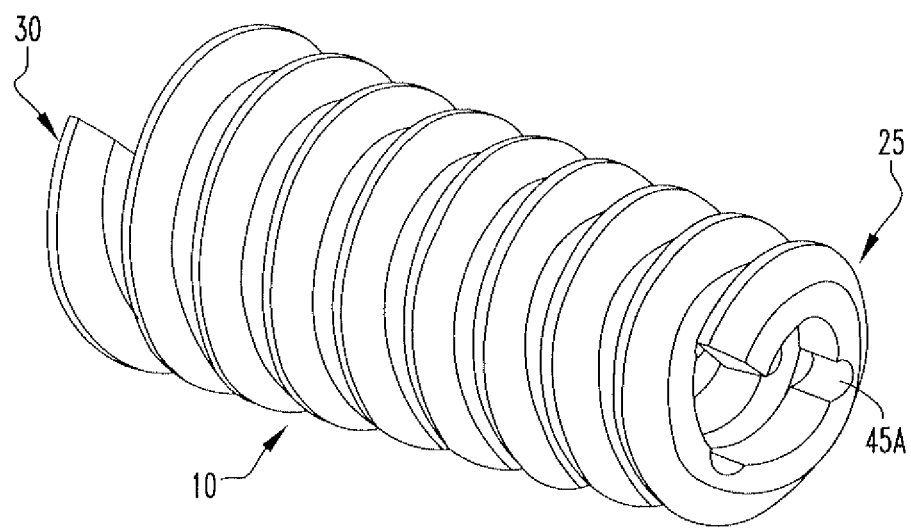
FIG. 39 is a schematic view showing a ninth helicoil interference fixation system formed in accordance with the present invention.

As seen in FIG. 38, the period of turns 40 may change along the length of helicoil 10.

Additionally, if desired, helicoil 10 can be tapered between its distal end 25 and its proximal end 30.

Modifications

It will be appreciated that still further embodiments of the present invention will be apparent to those skilled in the art in view of the present disclosure. It is to be understood that the present invention is by no means limited to the particular constructions and method steps herein disclosed and/or shown in the drawings, but also comprises any modifications or equivalents within the scope of the invention.

What is claimed is:

1. A helicoil interference fixation system comprising:
an open helicoil comprising a plurality of turns defining an internal volume communicating with a region exterior to the open helicoil through a spacing between the plurality of turns of the open helicoil, the open helicoil terminating in a proximal end and a distal end, and at least one internal strut extending along an entire length of the open helicoil between the proximal end and the distal end of the open helicoil; and
an inserter for turning the open helicoil, the inserter comprising a shaft having a proximal end and a grooved distal end having at least one groove located thereon for receiving an entire length of the at least one strut, the inserter further comprising a tapered threaded portion extending distal from the grooved distal end;
the open helicoil being mounted on the inserter such that the at least one strut of the open helicoil is captured by the at least one groove of the inserter, such that rotation of the inserter causes rotation of the open helicoil;
wherein the open helicoil comprises a tapered interior surface, and the inserter comprises a tapered exterior surface so that when the open helicoil is mounted on the inserter, the open helicoil and the inserter form a positive seat such that the tapered interior surface of the open helicoil is in direct contact with the tapered exterior surface of the inserter.

2. A system according to claim 1 wherein the open helicoil comprises at least two struts.

3. A system according to claim 1 wherein the distal end of the open helicoil is blunt.

4. A system according to claim 1 wherein there are at least two open helicoils.

5. A system according to claim 1 wherein the open helicoil is made out of a non-absorbable material.

6. A system according to claim 1 wherein the open helicoil is made out of an absorbable material.

7. A system according to claim 1 wherein the tapered threaded portion is configured to form a seat in tissue for receiving the turns of the open helicoil.

8. A system according to claim 7 wherein a portion of the tapered seat-forming thread is matched to the distal end of the open helicoil so that when the open helicoil is mounted on the inserter, the portion of the tapered seat-forming thread provides the proper lead-in for the distal end of the open helicoil.

\* \* \* \* \*